(12) United States Patent
Ueda et al.

(10) Patent No.: US 6,403,336 B1
(45) Date of Patent: Jun. 11, 2002

(54) PROCESS FOR THE PRODUCTION OF α-HUMAN ATRIAL NATRIURETIC POLYPEPTIDE

(75) Inventors: Ikuo Ueda, Toyonaka; Mineo Niwa, Mukou; Yoshimasa Saito, Osaka; Hisashi Yamada, Kawanishi; Yoshinori Ishii, Suita, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 08/370,356

(22) Filed: Jan. 9, 1995

Related U.S. Application Data

(63) Continuation of application No. 08/073,043, filed on Jun. 8, 1993, now abandoned, which is a continuation of application No. 07/385,952, filed on Jul. 28, 1989, now abandoned, which is a continuation of application No. 06/875,880, filed on Jun. 18, 1986, now abandoned.

(30) Foreign Application Priority Data

Jun. 20, 1985 (GB) .............................................. 8515686
Jan. 14, 1986 (GB) .............................................. 8600754

(51) Int. Cl.$^7$ ......................... C12P 21/02; C12N 15/03; C12N 15/11

(52) U.S. Cl. ...................... 435/69.7; 435/471; 435/476; 435/69.1; 435/320.1; 435/252.3; 435/252.33; 435/91.4; 435/91.1; 435/91.41; 536/23.1; 536/23.4; 536/23.2; 536/23.5; 536/23.51; 536/23.52; 536/24.1; 536/23.7; 536/24.2

(58) Field of Search .............................. 536/23.1, 23.4, 536/23.2, 23.5, 23.51, 23.52, 24.1, 23.7, 24.2; 435/320.1, 172.3, 252.3, 252.33, 91.4, 91.1, 91.41, 849, 10, 9, 13, 22, 27, 29, 73, 60, 69.7, 471, 476, 69.1

(56) References Cited

U.S. PATENT DOCUMENTS

| | | | | |
|---|---|---|---|---|
| 4,617,149 A | * | 10/1986 | DiMarchi et al. | ........... 530/324 |
| 4,745,179 A | * | 5/1988 | Ueda et al. | ................. 530/350 |
| 4,851,349 A | * | 7/1989 | Nakanishi et al. | ..... 435/252.33 |
| 5,019,500 A | * | 5/1991 | Ueda et al. | ................ 435/69.1 |
| 5,118,615 A | * | 6/1992 | Matsuo et al. | ............. 435/69.1 |

FOREIGN PATENT DOCUMENTS

| | | |
|---|---|---|
| EP | 0 001 929 | 5/1979 |
| EP | 0 131 363 | 1/1985 |
| EP | 0 152 333 | 8/1985 |
| EP | 0 159 943 | 10/1985 |
| EP | 0 164 273 | 12/1985 |
| EP | 0 206 769 | 12/1986 |
| WO | 85/04870 | 11/1985 |

OTHER PUBLICATIONS

Day, R.A. 1983. in: How To Write and Publish a Scientific Paper, Second Edition, ISI Press., Philadelphia, PA. pp. 15–19.*
Masaki et al. 1981 Biochem. Biophys. Acta. 660, 51–55.*
Gerhardt et al. 1981. in: *Manual of Methods for General Bacteriology,* Am. Soc. Microbiol., Washington D.C. pp. 156–157.*
*Enzyme Nomenclature,* 1984 (Webb, D., et al.) Academic Press., Orlando, pp. 270–533.*
Gray et al., 1982. Nature. 295, 593–598.*
Buell et al., 1985. Nuc. Acids Res. 13, 1923–1938.*
Watson, J.D. 1987. in: *Molecular Biology of the Gene.* $3^{rd}$ Edition. Benjamin/Cummings Publ. Co. Inc. CA. p. 313.*
Saito et al., 1987. J. Biochem. 102, 111–122.*
Stryer, L. 1975. in: *Biochemistry.* W H Freeman & Co. San Francisco. p. 636.*
Maruyama et al. 1986 Nuc. Acids Res. Supplement. 14, r151–R197.*
Weinstock et al. 1983. Proc. Natl. Acad. Sci. USA 80, 4432–4436.*
Gramtham et al. 1981 Nuc. Acids Res. 9, r43–r74.*
Mikuni et al. 1985, Siekagaku 57, 854. English translation relied upon.*
Hase et al. 1984, FEBS Letters 166, 39–43.*
Isemura et al. 1984, J. Biochem. 96, 489–498.*
Yoshida et al. 1984, FEBS Letters 170, 135–138.*
Allen et al. 1985, J. Cell Sci. Suppl. 3, 29–38.*
Houmard et al. 1972, Proc. Natl. Acad. Sci. USA 69, 3506–3509.*
Takamatsu et al. 1984, 7th Annual Meeting of Molecular Biology Society of Japan, (Dec. 4–7) p. 45, abstract No. B72, English translation relied upon.*
Communication of a Notice of Opposition in European Patent 0 206 769 B1, May 18, 1993.
Letter of Opposition of EP–B1 0 206 769, May 12, 1993.
S. Oikawa et al, *Nature,* vol. 309, pp. 724–726, (1984).
B. Greenberg et al, *Nature,* vol. 312, pp. 656–658 (1984).
M. Nemer et al, *Nature,* vol. 312, pp. 654–656 (1984).
K. Maeda et al, *Biochimica et Biophysica Acta,* vol. 828, pp. 222–228 (1985).
T. Miyata et al, *The Journal of Biological Chemistry,* vol. 259, pp. 8924–8933 (1984).
Reply Brief of Patentee in Japanese Patent Application 61–141900, Jul. 29, 1991.
Partial Translation of Reply Brief of Patentee Filed Jul. 29, 1991 for Japanese Patent Application No. 61–141900.

(List continued on next page.)

*Primary Examiner*—Christopher S. F. Low
(74) *Attorney, Agent, or Firm*—Oblon, Spivak, McClelland, Maier & Neustadt, P.C.

(57) ABSTRACT

DNA fragments which contain a sequence of DNA which encodes a protective peptide-fused α-hANP in which the protective peptide has a C-terminus lysine residue which is directly fused to the N-terminus of the α-hANP, vectors which contain such a DNA sequence, and microorganisms transformed which such a vector are useful for the production of α-hANP.

12 Claims, 20 Drawing Sheets

OTHER PUBLICATIONS

Figure 6:
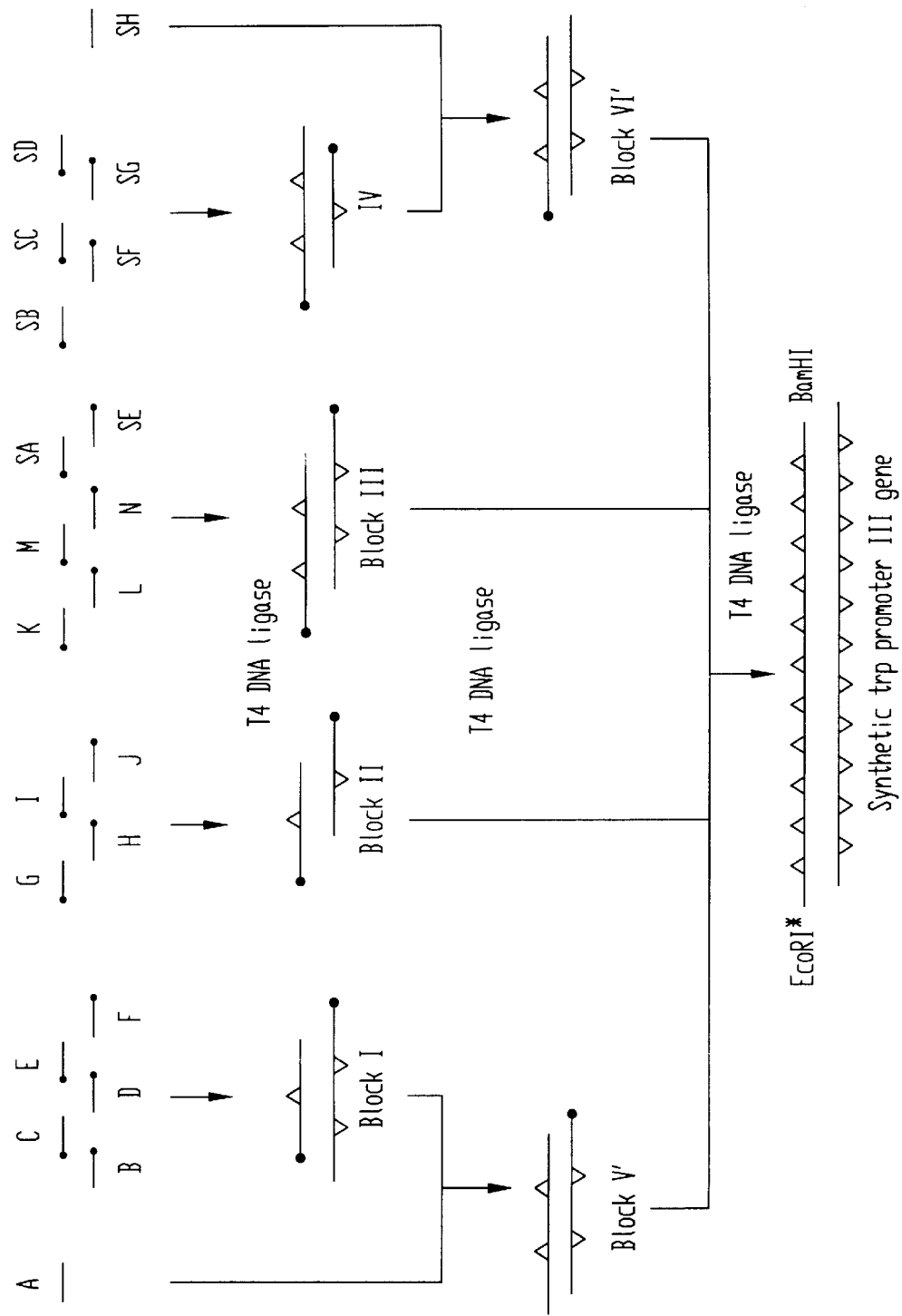

Patentees Reply to Opposition in European Patent No. 0 206–769 Fujisawa Pharmaceutical Co., Ltd.—Opposition by Suntory Limited, pp. 1–8, Dec. 16, 1993 (With Appendix I).

Brief Communication in European Patent No. 0 206 769, Jul. 11, 1994.

Opponents Observations in Response to the Observations of the Patentee, Opposition to EP–B1 0 206 769, Jul. 1, 1994.

Translation of Reply Brief of Patentee Filed Jul. 29, 1992, Opposition to Japanese Patent Application 61–141900.

F. Marston, *Biochem. J.,* vol. 240, pp. 1–12 (1986).

Translation of Seikagaku, vol. 57, Published Aug. 25, 1985, "2B–p1 Isolation of Recombinant Human Cardionatrin from *E. Coli*" S. Kanaya et al.

Experimental Report, Purpose: To Determine Whether α–hANP can be Liberated from a Chimeric Protein Comprising a Protective Peptide and αhANP Linked Through Glu By V8 Protease, pp. 1–9, Filed by Suntory in Opposition to European Patent No. 0 206 769 filed Jul. 1, 1994.

Decision of the Technical Board of Appeal 3.3.1 of Feb. 14, 1989 in Opposition to European Patent Application 83 870 003.7.

Letter from Dr. Hans–Rainer Jaenichen is Opposition to European Patent No. 0 206 769, Jul. 21, 1994.

Petition in Opposition to European Patent No. 0 206 769, Jul. 21, 1994.

P. Seeburg et al, *Nature,* vol. 276, pp. 795–798 (1978).

D. Goeddel et al, *Nature,* vol. 281, pp. 544–548 (1979).

D. Goeddel et al, *Proc. Natl. Acad. Sci. USA,* vol. 76, pp. 106–110 (1979).

K. Itakura et al, *Science,* vol. 198, pp. 1056–1063 (1977).

M. Courtney et al, *Proc. Natl. Acad. Sci. USA,* vol. 81, pp. 669–673 (1984).

Revocation of European Patent No. 0 206 769 Under Art. 102(1) or Art. 102(3) EPC, Jan. 23, 1995.

Provision of a Copy of the Minutes in European Patent No. 0 206 769 Under Rule 76(4) EPC, Jan. 23, 1995.

Statement of the Grounds of Appeal (Case No. T0202/95–334) in Opposition to European Patent No. 0 206 769, May 22, 1995.

Patentees' Further Submissions in Opposition to European Patent No. 0 206 769, Jan. 4, 1995.

Response to Opposition in Opposition to Japanese Patent Application 61–141900, Mar. 11, 1994.

T. Yonezu et al, *FEBS Letters,* vol., 203, pp. 149–152 (1986).

*Methods in Enzymology,* "Proteolytic Enzymes: Serine and Cysteine Peptidases", vol. 244, pp. 126–137, Ed. A. Barrett (1994).

Letter by Robert J. Gaunt in Opposition to European Patent No. 0 206 769, Jan. 3, 1997.

Nikkei Biotech, p. 3, Apr. 24, 1989, with Certified English Language Translation.

Nikkei Biotech, p. 3, Mar. 27, 1995, with Certified English Language Translation.

Nikkei Biotech, p. 3, Sep. 9, 1985, with Certified English Language Translation.

S. Tanaka et al, *Tanppakushitsu, Kakusan, Koso,* vol. 35, pp. 2613–2619 (1990) with English Language Translation.

J. Knott et al, *Eur. J. Biochem.,* vol. 174, pp. 405–410 (1988).

PG 45 of the Program and Abstract of the $7^{th}$ Annual Meeting of Molecular Biology Society of Japan, Dec. 4–7, 1984 with English Language Translation.

Isolation and Purification of α–Human Atrial Natriuretic Polypeptide (α–hANP), pp. 1–2, Feb. 9, 1996. Yoshimasa Saito.

Isolation and Purification of α–Human Atrial Natriuretic Polypeptide (α–hAMP), pp. 1–2.

Decision, Case No. T 0292/85, Date of Decision: Jan. 27, 1988.

Decision, Case No. T 0293/85, Date of Decision: Jan. 27, 1988.

Letter of the Opponent Opposition to European Patent No. 0 206 769, Oct. 16, 1995.

*Enzyme Nomenclature,* Academic Press, New York, pp. 388–389 and 398–399, (1992).

*Eur. J. Biochem,* "The Isolation and Characterisation of Human Atrial Natriuretic Factor Produced as a Fusion Protein in *Escherichia Coli*", vol. 174, pp. 405–410, (1988).

C.W. Dykes et al, *Eur. J. Biochem.,* "Expression of Atrial Natriuretic Factor as a Cleavable Fusion Protein with Chloramphenicol Acetyltransferase in *Esherichi Coli*", vol. 174, pp. 411–416, (1988).

Tanpakushitsu, Kakusan, Koso, vo. 35, pp. 2613–2619, (1990) (with English Translation).

* cited by examiner

EcoRI*
5'-AATTTGCCGACATCATAACGGTTCTGGCAAATATTCTGAAATGAGC-
3'-    ACGGCTGTAGTATTGCCAAGACCGTTTATAAGACTTTACTCG-

TGTTGACAATTAATCATCGAACTAGTTAACTAGTACGCAAGTTCACGTAAA-
ACAACTGTTAATTAGTAGCTTGATCAATTGATCATGCGTTCAAGTGCATTT-

EcoRI
AAGGGTATCG-3'
TTCCCATAGCTTAA-5'

*FIG. 1*

EcoRI*
5'- AATTTGCCGACATCATAACGGTTCTGGCAAATATTCTGAAATGAGC-
3'-    ACGGCTGTAGTATTGCCAAGACCGTTTATAAGACTTTACTCG-

TGTTGACAATTAATCATCGAACTAGTTAACTAGTACGCAAGTTCACGTAAA-
ACAACTGTTAATTAGTAGCTTGATCAATTGATCATGCGTTCAAGTGCATTT-

EcoRI
AAGGGTATCGAATTCATGGCTGGTTGTAAGAACTTCTTTTGGAAGACTTTC-
TTCCCATAGCTTAAGTACCGACCAACATTCTTGAAGAAAACCTTCTGAAAG-

BamHI
ACTTCGTGTTGATAG-3'
TGAAGCACAACTATCCTAG-5'

*FIG. 2*

*
EcoRI
5'-AATTTGCCGACATCATAACGGTTCTGGCAAATATTCTGAAATGAGCTGTTGACAATTAATCATCGAACTAGTTAAC-
3'-    ACGGCTGTAGTATTGCCAAGACCGTTTATAAGACTTTACTCGACAACTGTTAATTAGTAGCTTGATCAATTG-

ClaI
      TAGTACGCAAGTTCACGTAAAAAGGGTAT -3'
      ATCATGCGTTCAAGTGCATTTTTCCCATAGC -5'

*FIG. 3*

```
                                              (10)
                 Met Phe Tyr Phe Asn Lys Pro Thr Gly Tyr Gly Ser Ser Ser Arg Arg

Coding:      5'-ATG TTC TAC TTC AAC AAA CCG ACC GGC TAT GGC TCC AGC TCT CGT CGC
    Noncoding:   3'-TAC AAG ATG AAG TTG TTT GGC TGG CCG ATA CCG AGG TCG AGA GCA GCG

(20)                                    (30)
Ala Pro Gln Thr Gly Ile Val Asp Glu Gly Gly Asp Glu Phe Met Cys Tyr Cys Gln Asp Pro Tyr

GCA CCG CAG ACT GGT ATC GTA GAC GAG GGT GGC GAT GAA TTC ATG TGT TAC TGC CAG GAC CCA TAT
CGT GGC GTC TGA CCA TAG CAT CTG CTC CCA CCG CTA CTT AAG TAC ACA ATG ACG GTC CTG GGT ATA

(40)                              (50)                              (60)
Val Lys Glu Ala Glu Asn Leu Lys Lys Tyr Phe Asn Ala Gly His Ser Asp Val Ala Asp Asn Gly

GTA AAA GAA GCA GAA AAC CTT AAG AAA TAC TTT AAT GCA GGT CAT TCA GAT GTA GCG GAT AAT GGA
CAT TTT CTT CGT CTT TTG GAA TTC TTT ATG AAA TTA CGT CCA GTA AGT CTA CAT CGC CTA TTA CCT

(70)                              (80)
Thr Leu Phe Leu Gly Ile Leu Lys Asn Trp Lys Glu Glu Ser Asp Arg Lys Ile Met Gln Ser Gln
190
ACT CTT TTC TTA GGC ATT TTG AAG AAT TGG AAA GAG GAG AGT GAC AGA AAA ATA ATG CAG AGC CAA
TGA GAA AAG AAT CCG TAA AAC TTC TTA ACC TTT CTC CTC TCA CTG TCT TTT TAT TAC GTC TCG GTT

(90)                              (100)
Ile Val Ser Phe Tyr Phe Lys Leu Glu Val Glu His Glu Phe Gly Met Gly Gly Glu Ala Lys

ATT GTC TCC TTC TAC TTC AAG CTT GAA GTT GAG CAT GAA TTC GGT ATG GGC GGT GAA GCT AAA
TAA CAG AGG AAG ATG AAG TTC GAA CTT CAA CTC GTA CTT AAG CCA TAC CCG CCA CTT CGA TTT
```

*FIG. 4*

```
                                                                              1
           Lys Leu Glu Val Glu His Glu Phe Gly Met Gly Gly Glu Ala Lys Ser Leu Arg
           |──         linker DNA                              ──|
Coding:    5'-AG CTT GAA GTT GAG CAT GAA TTC GGT ATG GGC GGT GAA GCT AAA TCT CTG CGT
Noncoding:    3'-A CTT CAA CTC GTA CTT AAG CCA TAC CCG CCA CTT CGA TTT AGA GAC GCA
           (HindIII)

10                                           20
Arg Ser Ser Cys Phe Gly Gly Arg Met Asp Arg Ile Gly Ala Gln Ser Gly Leu Gly Cys Asn
                                 α-hANP gene
AGA TCC TCT TGC TTT GGT GGC CGT ATG GAC CGC ATC GGT GCT CAG TCC GGT CTG GGC TGT AAC
TCT AGG AGA ACG AAA CCA CCG GCA TAC CTG GCG TAG CCA CGA GTC AGG CCA GAC CCG ACA TTG 28
Ser Phe Arg Tyr ter ter (BamHI)
             |──
TCT TTC CGT TAC TGA TAG-3'
AGA AAG GCA ATG ACT ATC CTA G-5'
```

*FIG. 5*

```
             (HpaI)                                           (ClaI)      Met Phe Tyr Phe Asn
Coding:    5'-AAC TAG TAC GCA AGT TCA CGT AAA AAG GGT ATC GAT AAA ATG TTC TAC TTC AAC
Noncoding: 3'-TTG ATC ATG CGT TCA AGT GCA TTT TTC CCA TAG CTA TTT TAC AAG ATG AAG TTG
           |—a part of DNA fragment of synthetic trp                    |—
              promoter III
```
Lys Pro Thr Gly Tyr Gly Ser Ser Ser Arg Arg Ala Pro Gln Thr Gly Ile Val Asp Glu Gly Gly

```
AAA CCG ACC GGC TAT GGC TCC AGC TCT CGT CGC GCA CCG CAG ACT GGT ATC GTA GAC GAG GGT GGC
TTT GGC TGG CCG ATA CCG AGG TCG AGA GCA GCG CGT GGC GTC TGA CCA TAG CAT CTG CTC CCA CCG
                                peptide Cd gene
```

(EcoRI)
Asp Glu Phe (Met)
GAT G-3'
CTA CTT AA-5'
←|

*FIG. 12*

```
                                              (10)
                    Met Phe Tyr Phe Asn Lys Pro Thr Gly Tyr Gly Ser Ser Ser Arg Arg

Coding:      5'-ATG TTC TAC TTC AAC AAA CCG ACC GGC TAT GGC TCC AGC TCT CGT CGC
Noncoding:   3'-TAC AAG ATG AAG TTG TTT GGC TGG CCG ATA CCG AGG TCG AGA GCA GCG

(20)                                         (30)
Ala Pro Gln Thr Gly Ile Val Asp Glu Gly Gly Asp Glu Phe Met Cys Tyr Cys Gln Asp Pro Tyr

GCA CCG CAG ACT GGT ATC GTA GAC GAG GGT GGC GAT GAA TTC ATG TGT TAC TGC CAG GAC CCA TAT
CGT GGC GTC TGA CCA TAG CAT CTG CTC CCA CCG CTA CTT AAG TAC ACA ATG ACG GTC CTG GGT ATA

(40)                              (50)                                    (60)
Val Lys Glu Ala Glu Asn Leu Lys Lys Tyr Phe Asn Ala Gly His Ser Asp Val Ala Asp Asn Gly

GTA AAA GAA GCA GAA AAC CTT AAG AAA TAC TTT AAT GCA GGT CAT TCA GAT GTA GCG GAT AAT GGA
CAT TTT CTT CGT CTT TTG GAA TTC TTT ATG AAA TTA CGT CCA GTA AGT CTA CAT CGC CTA TTA CCT

(70)                                    (80)
Thr Leu Phe Leu Gly Ile Leu Lys Asn Trp Lys Glu Glu Ser Asp Arg Lys Ile Met Gln Ser Gln

ACT CTT TTC TTA GGC ATT TTG AAG AAT TGG AAA GAG GAG AGT GAC AGA AAA ATA ATG CAG AGC CAA
TGA GAA AAG AAT CCG TAA AAC TTC TTA ACC TTT CTC CTC TCA CTG TCT TTT TAT TAC GTC TCG GTT

(90)                                    (100)
Ile Val Ser Phe Tyr Phe Lys Leu Glu Val Glu His Glu Phe Gly Met Gly Gly Glu Ala Lys Ser

ATT GTC TCC TTC TAC TTC AAG CTT GAA GTT GAG CAT GAA TTC GGT ATG GGC GGT GAA GCT AAA TCT
TAA CAG AGG AAG ATG AAG TTC GAA CTT CAA CTC GTA CTT AAG CCA TAC CCG CCA CTT CGA TTT  AGA (110)                                (120)
Leu Arg Arg Ser Ser Cys Phe Gly Gly Arg Met Asp Arg Ile Gly Ala Gln Ser Gly Leu Gly Cys

CTG CGT AGA TCC TCT TGC TTT GGT GGC CGT ATG GAC CGC ATC GGT GCT CAG TCC GGT CTG GGC TGT
GAC GCA TCT AGG AGA ACG AAA CCA CCG GCA TAC CTG GCG TAG CCA CGA GTC AGG CCA GAC CCG ACA (130)
Asn Ser Phe Arg Tyr

AAC TCT TTC CGT TAC -3'
TTG AGA AAG GCA ATG -5'
```

FIG. 17

PROCESS FOR THE PRODUCTION OF α-HUMAN ATRIAL NATRIURETIC POLYPEPTIDE

This application is a Continuation of application Ser. No. 08/073,043, filed on Jun. 8, 1993 now abandoned which was a Continuation of application Ser. No. 07/385,952, filed on Jul. 28, 1989 now abandoned which was a Continuation of application Ser. No. 06/875,880, filed on Jun. 18, 1986 now abandoned.

This invention relates to a new process for the production of α-human atrial natriuretic polypeptide (hereinafter referred to as the abbreviation "α-hANP") by recombinant DNA technology. More particularly, it relates to a new process for the production of α-hANP by recombinant DNA technology, to chemically synthesized genes for α-hANP and protective peptide-fused α-hANP and to a corresponding recombinant vector and transformant comprising the same.

The α-hANP is a known polypeptide having a diuretic, natriuretic, vasorelaxant and antihypertensive activities Therefore, it may be useful in clinical treatment of hypertension as antihypertensive diuretic agent and has the following structure:

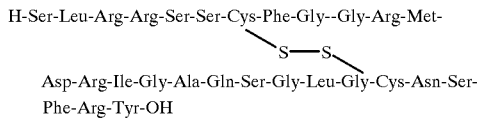

(I)

H-Ser-Leu-Arg-Arg-Ser-Ser-Cys-Phe-Gly--Gly-Arg-Met-
Asp-Arg-Ile-Gly-Ala-Gln-Ser-Gly-Leu-Gly-Cys-Asn-Ser-Phe-Arg-Tyr-OH (Cf. Biochemical and Biophysical Research Communications Vol.118, page 131 (1984)).

The inventors of this invention have newly created a process for the production of α-hANP by recombinant DNA technique using an expression vector comprising a synthetic gene encoding the amino acid sequence (I) of α-hANP. According to this process, α-hANP can be obtained in high yield.

This invention provide a process for the production of α-hANP by (1) culturing a microorganism transformed with an expression vector comprising a synthetic gene encoding an amino acid sequence of a protective peptide-fused α-hANP in a nutrient medium, (2) recovering the protective peptide-fused α-hANP from the cultured broth and (3) removing the protective peptide part of the protective peptide-fused α-hANP.

In the above process, particulars of which are explained in more detail as follows.

The microorganism is a host cell and may include bacteria, fungi, cultured human and animal cells and cultured plant cells. Preferred examples of the microorganism may include bacteria especially a strain belonging to the genus Escherichia (e.g. E. coli HB101 (ATCC 33694), E. coli 294 (ATCC 31446), E. coli (1776) (ATCC 31537), etc).

The expression vector is usually composed of DNA having at least a promoter-operater region, initiation codon, synthetic protective peptide gene, synthetic α-hANP gene, termination codon(s) and replicatable unit.

The promoter-operater region comprises promoter, operater and Shine-Dalgarno(SD) sequence (e.g. AAGG, etc.). The distance between SD sequence and initiation codon is preferably 8–12 b.p. and in the most preferable case as shown in the working Examples mentioned below, the distance between SD sequence and initiation codon (ATG) is 11 b.p. Examples of the promoter-operater region may include conventionally employed promoter-operater region (e.g. lactose-operon, PL-promoter, trp-promoter, etc.) as well as synthetic promoter-operater region. Preferred examples of the promoter-operater region are synthetic trp promoter I, II and III which were newly synthesized by the inventors of this invention and DNA sequences thereof are shown in FIG. 1, 2 and 3, respectively. In the process,there may be used 1–3 consecutive promoter-operater region(s) per expression vector.

Preferred initiation codon may include methionine codon (ATG).

The protective peptide gene may include DNA sequence corresponding to any of peptide or protein which is capable of forming a fused protein with α-hANP and inhibiting undesired degradation of the fused protein in the host cell or the cultured broth. One of preferred examples is "peptide Cd gene" linked to "LH protein gene" (hereinafter "the peptide Cd gene linked to LH protein gene" is referred to as "peptide CLa gene"), DNA sequence of which is shown in FIG. 4.

The DNA sequence of α-hANP gene is designed from the amino acid sequence of α-hANP, subjected to a number of specific non-obvious criteria. Preferred example of DNA sequence of α-hANP gene is shown in FIG. 5. In the working Examples as mentioned below, between the α-hANP gene and the protective peptide gene, a DNA sequence encoding amino acid lysine is inserted, with the purpose of Achromobacter protease I digestion at the junction of the fused protein.

The termination codon(s) may include conventionally employed termination codon (e.g. TAG, TGA, etc.).

The replicatable unit is a DNA sequence capable of replicating the whole DNA sequence belonging thereto in the host cells and may include natural plasmid, artificially modified plasmid (e.g. DNA fragment prepared from natural plasmid) and synthetic plasmid and preferred examples of the plasmid may include plasmid pBR 322 or artificially modified thereof (DNA fragment obtained from a suitable restriction enzyme treatment of pBR 322). The replicatable unit may contain natural or synthetic terminator (e.g. synthetic fd phage terminator, etc.).

Synthetic preparation of promoter-operater region, initiation codon,protective peptide gene, α-hANP gene and termination codon can be prepared in a conventional manner as generally employed for the preparation of polynucleotides.

The promoter-operater region, initiation codon, protective peptide gene, α-hANP gene and termination codon(s) can consecutively and circularly be linked with an adequate replicatable unit (plasmid) together, if desired using an adequate DNA fragment(s) (e.g. linker, other restriction site , etc.) in a conventional manner (e.g. digestion with restriction enzyme, phosphorylation using T4 polynucleotide kinase, ligation using T4 DNA-ligase) to give an expression vector.

The expression vector can be inserted into a microorganism (host cell). The insertion can be carried out in a conventional manner (e.g. transformation, microinjection, etc.) to give a transformant.

For the production of α-hANP in the process of this invention, thus obtained transformant comprising the expression vector is cultured in a nutrient medium.

The nutrient medium contains carbon source(s) (e.g. glucose, glycerine, mannitol, fructose, lactose, etc.) and inorganic or organic nitrogen source(s) (ammonium sulfate, ammonium chloride, hydrolysate of casein, yeast extract, polypeptone, bactotrypton, beef extracts, etc.). If desired, other nutritious sources (e.g. inorganic salts (e.g. sodium or potassium biphosphate, dipotassium hydrogen phosphate, magnesium chloride, magnesium sulfate, calcium chloride), vitamins (e.g. vitamin B1), antibiotics (e.g. ampicillin), etc.) may be added to the medium.

The culture of transformant may generally be carried out at pH 5.5–8.5 (preferably pH 7–7.5) and 18–40° C. (preferably 25–38° C.) for 5–50 hours.

Since thus produced protective peptide-fused α-hANP generally exists in cells of the cultured transformant, the cells are collected by filtration or centrifuge, and cell wall and/or cell membrane thereof is destroyed in a conventional manner (e.g. treatment with super sonic waves and/or lysozyme, etc.) to give debris. From the debris, the protective peptide-fused α-hANP can be purified and isolated in a conventional manner as generally employed for the purification and isolation of natural or synthetic proteins (e.g. dissolution of protein with an appropriate solvent (e.g. 8M aqueous urea, 6M guanidine, etc.), dialysis, gel filtration, column chromatography, high performance liquid chromatography, etc.).

The α-hANP can be prepared by cleaving the protective peptide-fused α-hANP in the presence of an appropriate protease (e.g. Achromobacter Protease I (AP I), etc.) treatment or chemical method (e.g. treatment with cyanogen bromide). In the case where C-terminal of the protective peptide is lysine, there can preferably be employed treatment with API. Although API is a known enzyme (Cf. Biochim. Biophys. Acta., 660, 51 (1981)), it has never been reported that fused proteins prepared via recombinant DNA technology can preferably be cleaved by the treatment with API. This method may preferably be employed for cleaving a fused protein composed of peptides having a lysine between a protective peptide and a target peptide having no lysine in its molecule.

The cleavage of the fused protein may be carried out at pH 5–10 and 20–40° C. (preferably 35–40° C.) for 2–15 hours in an aqueous solution (e.g. buffer solution, aqueous urea, etc.).

In the working Examples as mentioned below, the fused protein is treated with API firstly in a buffer solution containing 8M urea at pH 5, secondly, in a buffer solution containing 4M urea at pH 9. In this condition, the fused protein is cleaved at lysine site, and the produced α-hANP is refolded spontaneously.

Thus produced α-hANP can be purified and isolated from the resultant reaction mixture in a conventional manner as mentioned above.

The Figures attached to this specification are explained as follows.

In the some of Figures, oligonucleotides are illustrated with the symbol ＿, •——— or ———• (in this symbol, the marks·means 5'-phosphorylated end by T4 polynucleotide kinase), and blocked oligonucleotides are illustrated with the symbol, ＿, •———, ———•, ▲, •▲ or ▲• (in this symbol, the mark Δ means ligated position).

In the DNA sequence in this specification. A. G. C and T mean the formula:

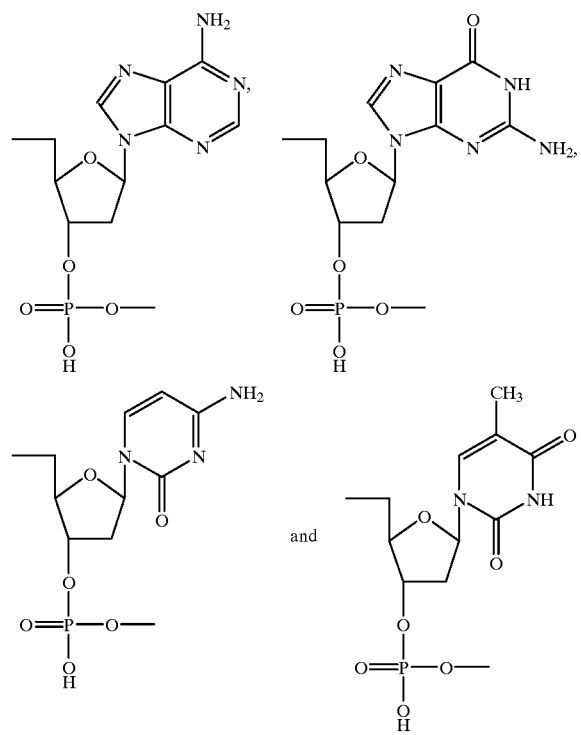

respectively, and

5'-terminal A, G, C and T mean the formula:

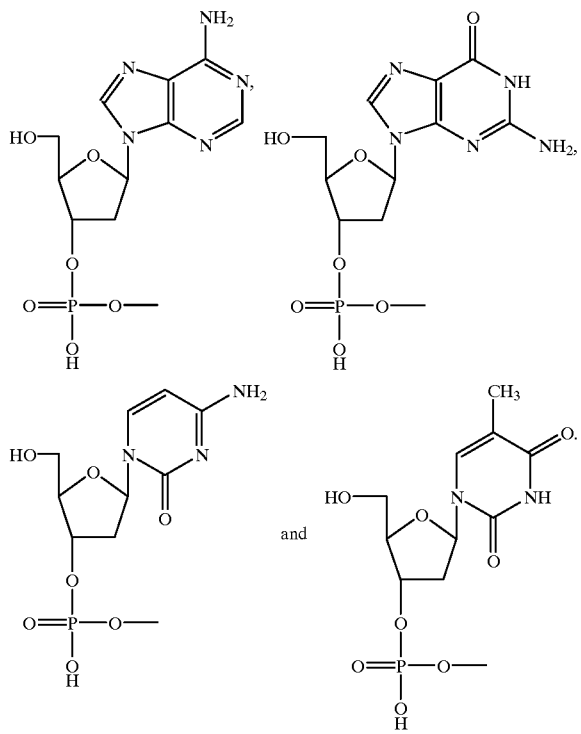

respectively, and 3-terminal A, G, C and I mean the formula;
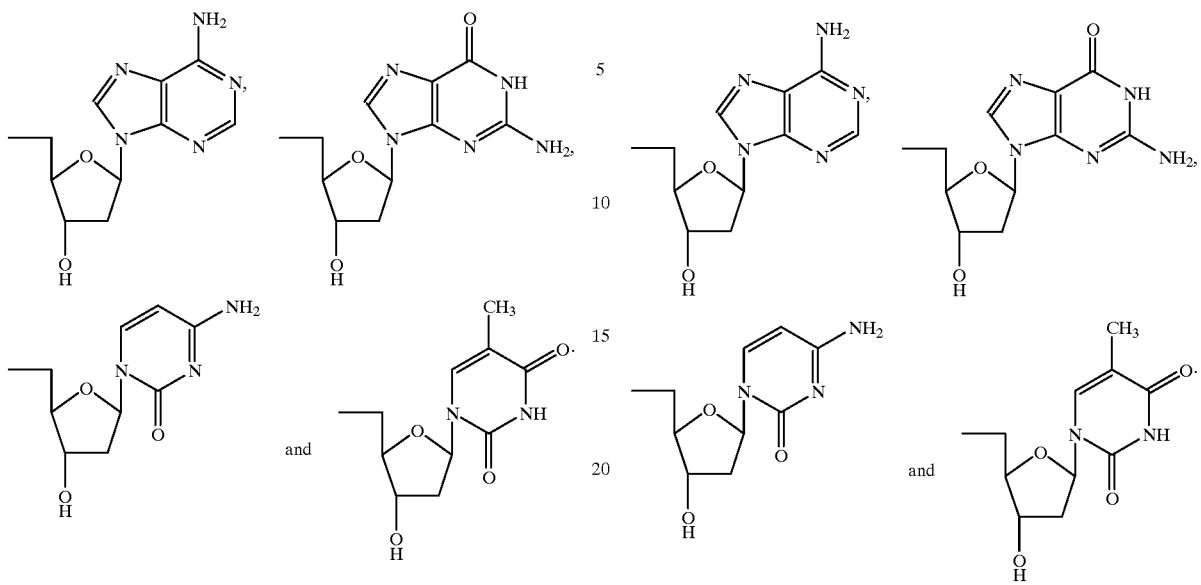
respectively, unless otherwise indicated.
In the following Examples, following abbreviations are used.
Ap, Gp, Cp and Ip mean the formula:
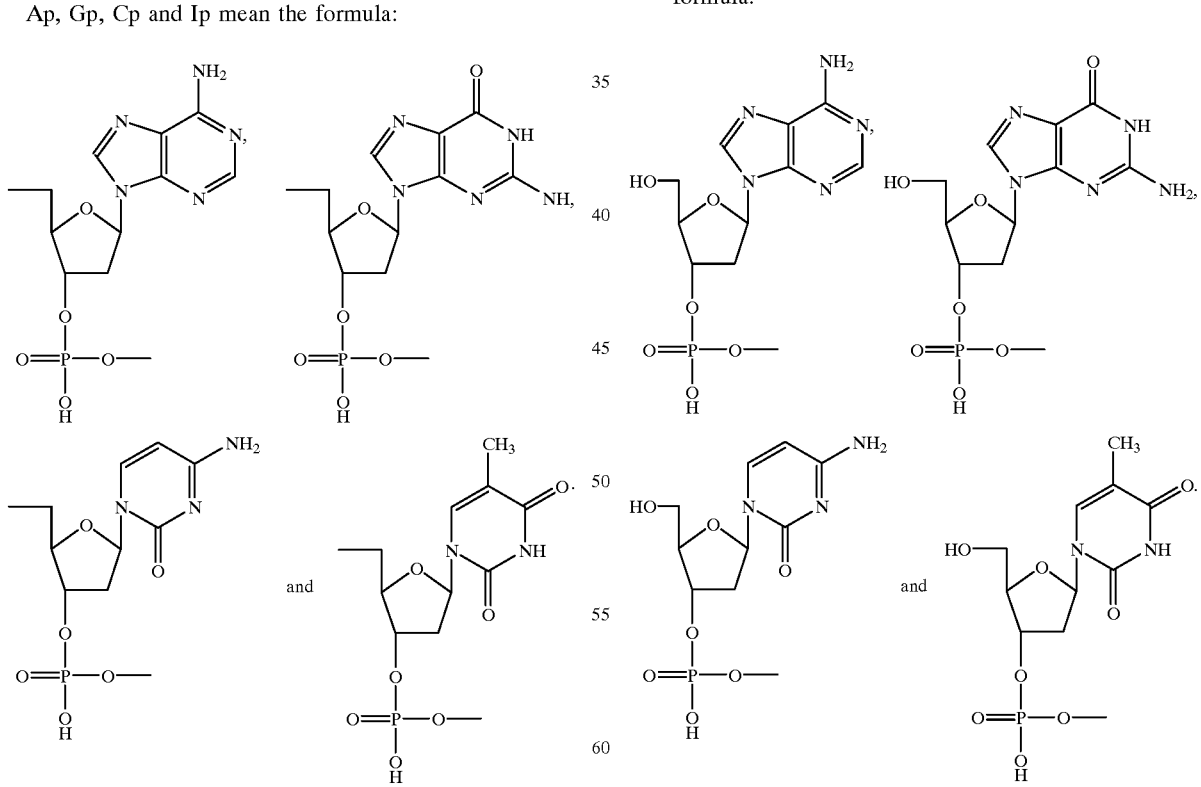
respectively, and
3'-terminal AOH, GOH, COH and IOH mean the formula:
respectively, and
5'-terminal HOAP, HOGP, HOCp and HOTP mean the formula:
respectively, and $A^{Bz}$po, $G^{iB}$po, $C^{Bz}$po, Tpo and TO mean the formula:

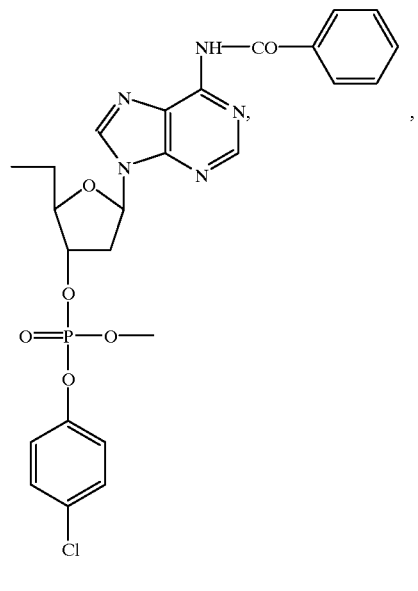

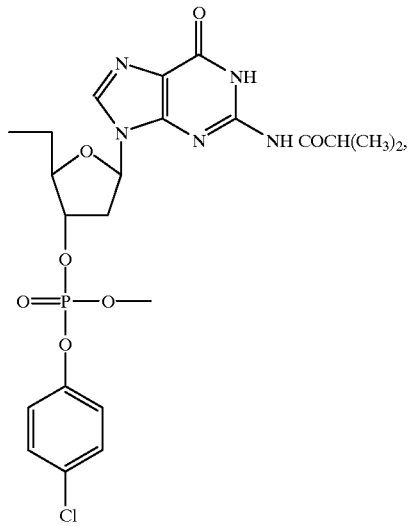

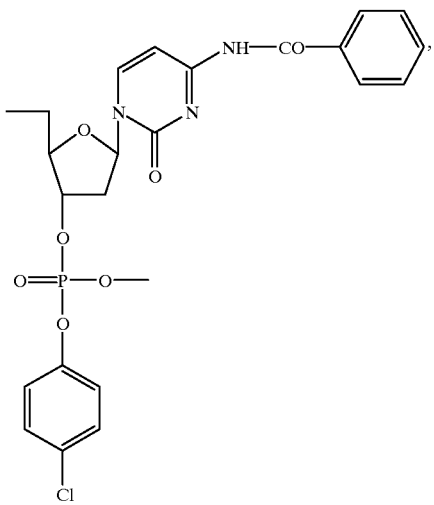

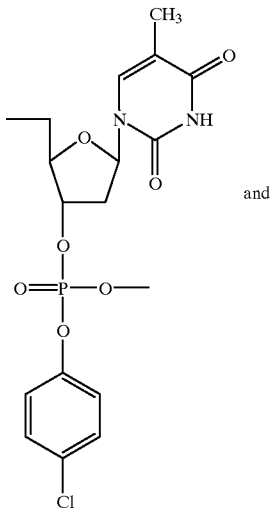

and

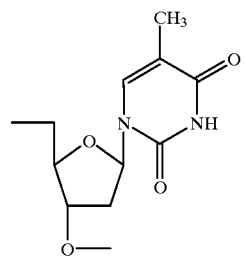

respectively, and

DMTR is dimethoxytrityl, and

CE is cyanoethyl.

Mono (or di, or tri)mer (of oligonucleotides) can be prepared by, for examples the Hirose's method [Cf. Tanpakushitsu Kakusan Kohso 25, 255 (1980)] and coupling can be carried out, for examples on cellulose or polystyrene polymer by a phosphotriester method [Cf. Nucleic Acid Research, 9, 1691 (1981), Nucleic Acid Research 10, 1755 (1982)].

The following Examples are given for the purpose of illustrating this invention, but not limited thereto.

In the Examples, all of the used enzymes (e.g. restriction enzyme, T4 polynucleotide kinase, T4 DNA ligase) are commercially available and conditions of usage of the enzymes are obvious to the person skilled in the art, for examples, referring to a prescription attached to commercially sold enzymes, Further, in the Examples, the term "polystyrene polymer" means aminomethylated polystyrene·HCl, divinylbenzene 1%, 100–200 mesh (sold by Peptide Institute Inc.)

EXAMPLE 1

Synthesis of
HOCpTpGpCpGpTpApGpApTpCpCpTpCpTOH
(AH7)

(1) Synthesis of DMTrOTpoC$^{Bz}$poTO-succinyl-polystyrene Polymer i) Preparation of HOTO-succinyl Polystyrene Polymer:

To a DMTrO-To -succinyl-polystyrene polymer (51.8 mg, 10.37 μmole) (prepared by the method described in Nucleic Acid Research 10, 1755 (1982)) in a reaction syringe, 5% dichloroacetic acid (DCA) solution in dichloromethane (2 ml) was added. After the standing for 1 minute, the mixture was filtered through filter glass by nitrogen gas. The DCA treatment was repeated more two times. The polymer was washed with dichloromethane (2 ml×3), methanol (2 ml×3) and pyridine (2 ml×3) succesively, and dried by nitrogen gas stream to give polymer adduct I.

ii) Preparation of DMTrOTpoC$^{Bz}$po-:

DMTrOTpoC$^{Bz}$po-CE (32.4 mg, 8.12 μmole) prepared by the method described in Tanpakushitsu Kakusan Kohso 25, 255 (1980) was treated with a mixture of triethylamine and acetonitrile (1:1 v/v, 5 ml) at room temperature for 30 minutes. The phosphodiester dimer (DMTrOTpoC$^{Bz}$po-) thus obtained was dried, water being separated as the pyridine azeotrope (2 ml×2).

iii) Coupling:

The dimer (DMTrOTpoC$^{Bz}$po-) and mesitylen sulfonylnitrothiazolide (MSNT) (80 mg) were dissolved in pyridine (0.5 ml). The solution was added into the reaction syringe with the polymer adduct I, and the mixture was shaked for 1 hour at room temperature. The reaction mixture was filtered through filter glass by nitrogen gas, and washed with pyridine (2 ml×3) to give the polymer adduct II.

iv) Acetylation of Unreacted 5'-hydroxy Groups:

To the polymer adduct II obtained as above, pyridine (0.9 ml) and acetic anhydride (0.1 ml) were added and the mixture was shaked for 15 minutes. Then the reaction solution was removed through filter glass and the resultant polymer was washed successively with pyridine (2 ml×3), methanol (2 ml×3) and dichloromethane (2 ml×3), and then dried by nitrogen gas stream. The polymer adduct (DMTrOTpoC$^{Bz}$poto-succinyl-polystyrene polymer) can use for the next coupling step.

(2) Synthesis of DMTrOTpoC$^{Bz}$poC$^{Bz}$poTpoC$^{Bz}$poTO-succinyl-polystyrene Polymer:

DMTrOTpoC$^{Bz}$poC$^{Bz}$poTpoC$^{Bz}$potO-succinyl-polystyrene polymer was synthesized from DMTrOTpoC$^{Bz}$poTO-succinyl-polystyrene polymer and DMTrOTpoC$^{Bz}$poC$^{Bz}$poCE (44.9 mg) according to similar conditions as above (1).

(3) Synthesis of DMTrOAzpoG$^{iB}$pOA$^{Bz}$BpOTpoC$^{Bz}$poC$^{Bz}$poTpo-C$^{Bz}$poTO-succinyl-polystyrene Polymer:

DMTrOA$^{Bz}$poG$^{iB}$poA$^{Bz}$poTpoC$^{Bz}$poC$^{Bz}$poTpoC$^{Bz}$poTO-succinyl-polystyrene polymer was synthesized from DMTrOTpoC$^{Bz}$poC$^{Bz}$poTpoC$^{Bz}$poTO-succinyl-polystyrene polymer and DMTrOA$^{Bz}$poG$^{iB}$poA$^{Bz}$poCE (48.5 mg) according to similar conditions as above (1).

(4) Synthesis of DMTrOC$^{Bz}$poG$^{iB}$poTpoA$^{Bz}$poG$^{iB}$poA$^{Bz}$poTpo-C$^{Bz}$poC$^{Bz}$poTpoC$^{Bz}$poTO-succinyl-polystyrene polymer:

DMTrOC$^{Bz}$poG$^{iB}$poTpoA$^{Bz}$poG$^{iB}$poA$^{Bz}$poTpoC$^{Bz}$poC$^{Bz}$poTpo-C$^{Bz}$poTO-succinyl-polystyrene polymer was synthesized from DMTrOA$^{Bz}$poG$^{Bz}$poA$^{Bz}$poTpoC$^{Bz}$poC$^{Bz}$poTpoC$^{Bz}$poTO-succinyl-polystyrene polymer and DMTrOC$^{Bz}$-poG$^{iB}$poTpoCE (45.1 mg) according to similar conditions as above (1).

(5) Synthesis of DMTrOC$^{Bz}$poTpoG$^{Bz}$poC$^{Bz}$poG$^{Bz}$-poTpoA$^{Bz}$poG$^{iB}$poA$^{Bz}$poTpoC$^{Bz}$poC$^{Bz}$popoC$^{Bz}$poTO-succinyl-polystyrene Polymer:

DMTrOC$^{Bz}$poTpoG$^{iB}$poC$^{Bz}$poG$^{iB}$poTpoA$^{Bz}$poG$^{iB}$po A$^{Bz}$poTpoC$^{Bz}$poC$^{Bz}$poTpoC$^{Bz}$poTO-succinyl-polystyrene polymer (60 mg) was synthesized from DMTrOC$^{Bz}$poG$^{iB}$-poTpoA$^{Bz}$poG$^{iB}$poA$^{Bz}$poTpoC$^{Bz}$poC$^{Bz}$po poC$^{Bz}$poTO-succinyl-polystyrene polymer and DMTrOC$^{Bz}$-poTpoG$^{iB}$poCE (45.1 mg) according to similar conditions as above (1). At this final step, unreacted 5'-hydroxy group was not necessary to protect with an acetyl group.

(6) Synthesis of HOCpTpGpCpGpTpApGpApTpCpCpT-pCpTOH:

DMTrOC$^{Bz}$poTpoG$^{iB}$poC$^{Bz}$poG$^{iB}$poTpoA$^{Bz}$poG$^{iB}$po A$^{Bz}$poTpoC$^{Bz}$poC$^{Bz}$poTpoC$^{Bz}$poTO-succinyl-polystyrene polymer (60 mg) was treated with 1M N,N,N',N'-tetramethylenequanidium pyridine 2-aldoximate (in dioxane-water (1:1: v/v, 1ml)) at 37° C. for 20 hours in a sealed tube. To the reaction mixture 28% (w/w) aqueous ammonia (12 ml) was added, and the mixture was heated at 60° C. for 5 hours. The solid polymer was removed by filtration and washed with water (10 ml). The filtrate and washed solution were evaporated to dryness, and the residue was treated with 80% aqueous acetic acid (25 ml) at room temperature for 15 minutes. After removal of the solvent, the residue was dissolved in 0.1M triethylammonium carbonate buffer (pH 7.5, 25 ml) was washed with diethylether (3×25 ml). Aqueous layer was evaporated to dryness and the residue was dissolved in 0.1M triethylammonium carbonate buffer (pH 7.5, 2 ml) to yield curde HOCpTpGpCpGpTpA-pGpApTpCpCpTpCpTOH in the solution.

(7) Purification of HOCpTpGpCpGpTpApGpApTpCpCpT-pCpTOH i) First purification of the crude product was performed by column chromatography on Biogel P2 (Biolad) (24×2.6 cm ID). The fractions corresponding to the first eluted peak (50 mM ammonium acetate containing 0.1 mM EDTA, flow rate: 1 ml/min) were collected and freeze-dried to give the first purified product.

ii) Second purification of the first purified product was performed by high performance liquid chromatography (HPLC) on CDR-10 (Mitsubishi Kasei) (25 cm×4.6 mm ID) using a linear gradient of 1M ammonium acetate-10% (v/v) aqueous ethanol to 4.5 M ammonium acetate-10% (v/v) aqueous ethanol (80 minutes, flow rate: 1 ml/minute, 60° C.) to give the second purified product.

iii) Third purification of the second purified product was performed by reverse phase HPLC (Rp-18-5 μ(×77) (Merck), 15 cm×4mm ID) using a linear gradient of 0.1 M ammonium acetate to 0.1 M ammonium acetate-15% (v/v) aqueous acetonitrile (40 minutes, 1.5 ml/minute, room temperature) to give the final purified product.

(HOCpTpGpCpGpTpApGpApTpCpCpTpCpTOH)

(8) Analysis of oligonucleotide:

(HOCpTpGpCpGpTpApGpApTpCpCpTpCpTOH)

i) Digestion by phosphodiesterase

The mixture of HOCpTpGpCpGpTpApGpApTpCpCpT-pCpTOH (10 μg, 5.1 μl), 0.2M MgCl$_2$ (20 μl), 0.2M tris-HCl (pH8.5) (20 μl) and 0.1 mM EDTA (144.9 μl) was treated with phosphodiesterase (10 unit, 10 μl) at 37° C. for 20 minutes, and then heated at 100° C. for 2 minutes.

ii) Analysis by HPLC:

The oligonucleotide in the reaction mixture was analyzed by HPLC (CDR-10 (Mitsubishi Kasei), 25 cm×4.6 mm ID) using a linear gradient of water to 2.0 M ammonium acetate (pH 3.4) (40 minutes, flow rate: 1.5 ml/minute, 60° C.). From each peak area observed, its nucleotide composition was determined comparing with area of a standard sample.

Calcd: pCOH 4.000, pAOH 2.000, pTOH 5.000, pGOH 3.000; Observed: pCOH 3.770, pAOH 2.026, pTOH 5.237, pGOH 2.968.

EXAMPLE 2

Synthesis of Oligonucleotide

Following oligonucleotides were prepared in a similar manner to that described in Example 1.

(1) HOApGpCpTpTpGpApApGpTpTpGpA-pGpCpApTpGOH (AH1)

(2) HOApApTpTpCpApTpGpCpTpCpApA-pCpTpTpCpAOH (AH2)

(3) HOApApTpTpCpGpGpTpApTpGpGpGpCOH (AH3)
(4) HOTpTpCpApCpCpGpCpCpCpApTpApCpCpGOH (AH4)
(5) HOGpGpTpGpApApGpCpTpApApApTpCpTOH (AH5)
(6) HOCpGpCpApGpApGpApTpTpTpApGpCOH (AH6)
(7) HOApApGpCpApApGpApGpGpGpApTpCpTpAOH (AH8)
(8) HOTpGpCpTpTpTpGpGpTpGpGpCpCpGpTOH (AH9)
(9) HOTpCpCpApTpApCpGpGpCpCpApCpCpAOH (AH10)
(10) HOApTpGpGpApCpCpGpCpApTpCpGpCpTOH (AH 1)
(11) HOTpGpApGpCpApCpCpGpApTpGpCpGpGOH (AH12)
(12) HOGpCpTpCpApGpTpCpCpGpGpTpCpTpGOH (AH13)
(13) HOCpApGpCpCpCpApGpApCpCpGpGpApCOH (AH14)
(14) HOGpGpCpTpGpTpApApCpTpCpTpTpTpCOH (AH15)
(15) HOTpApApCpGpGpApApApGpApGpTpTpAOH (AH16)
(16) HOCpGpTpTpApCpTpGpApTpApGOH (AH17)
(17) HOGpApTpCpCpTpApTpCpApGOH (AH18)

EXAMPLE 3

Synthesis of Oligonucleotides

Following oligonucleotides were prepared by a similar manner to that of Example 1.

(1) HOApApTpTpTpGpCpCpGpApCpAOH (A)
(2) HOCpGpTpTpApTpGpApTpGpTpCpGpGpCpAOH (B)
(3) HOTpCpApTpApApCpGpGpTpTpCpTpGpGpCOH (C)
(4) HOGpApApTpApTpTpTpGpCpCpApGpApApCOH (D)
(5) HOApApApTpApTpTpCpTpGpApApApTpGpAOH (E)
(6) HOTpCpApApCpApGpCpTpCpApTpTpTpCpAOH (F)
(7) HOGpCpTpGpTpTpGpApCpApApApTpTpApApTOH (G)
(8) HOGpTpTpCpGpApTpGpApTpTpApApApTpTpGOH (H)
(9) HOCpApTpCpGpApApApCpTpApGpTpTpApApCQH (I)
(10) HOGpCpGpTpApCpTpApGpTpTpApApCpTpAOH (J)
(11) HOTpApGpTpApCpGpCpApApGpTpTpCpApCOH (K)
(12) HOCpTpTpTpTpTpApCpGpTpGpApApCpTpTOH (L)
(13) HOGpTpApApApApApGpGpGpTpApTOH (MI')
(14) HOCpGpApTpApCpCpOH (N')
(15) HOGpTpApApApApApGpGpGpTpApTpCpGOH (M)

(16) HOApApTpTpCpGpApTpApCpCOH (N)
(17) HOApApTpTpCpApTpGpGpCpTOH (SA)
(18) HOGpGpTpTpGpTpApApGpApApCpTpTpCpTOH (SB)
(19) HOTpTpTpGpGpApApGpApCpTpTpTOH (SC)
(20) HOCpApCpTpTpCpGpTpGpTpTpGpApTpApGOH (SD)
(21) HOTpTpApCpApApCpCpApGpCpCpApTpGOH (SE)
(22) HOCpCpApApApApGpApApGpTpTpCOH (SF)
(23) HOCpGpApApGpTpGpApApApGpTpCpTpTOH (SG)
(24) HOGpApTpCpCpTpApTpCpApApCpAOH (SE)

EXAMPLE 4

Synthesis of Oligonucleotides

Following oligonucleotides were prepared by a similar manner to that of Example 1.

(1) HOApApCpTpApGpTpApCpGpCOH (Np1)
(2) HOApApCpTpTpGpCpGpTpApCpTpApGpTpTOH (Np4)
(3) HOApApGpTpTpCpApCpGpTpApApApApApGOH (Np2)
(4) HOApTpApCpCpCpTpTpTpTpTpApCpGpTpGOH (Np5)
(5) HOGpGpTpApTpCpGpApTpApApApApApTpGOH (Np3)
(6) HOGpTpApGpApApCpApTpTpTpTpApTpCpGOH (Np6)
(7) HOTpTpCpTpApCpTpTpCpApApCpApApAOH (Cd1)
(8) HOGpGpTpCpGpGpTpTpTpGpTpTpGpApAOH (Cd2)
(9) HOCpCpGpApCpCpGpGpCpTpApTpGOH (Cd3)
(10) HOGpCpTpGpGpApGpCpCpApTpApGpCpCOH (G2)
(11) HOGpCpTpCpCpApGpCpTpCpTpCpGpTpCOH (H1)
(12) HOCpGpGpTpGpCpGpCpGpApCpGpApGpAOH (H2)
(13) HOGpCpGpCpApCpCpGpCpApGpApCpTpGOH (I1)
(14) HOGpApTpApCpCpApGpTpCpTpGOH (Cd4)
(15) HOGpTpApTpCpGpTpApGpApCpGOH (Cd5)
(16) HOApCpCpCpTpCpGpTpCpTpApCOH (Cd6)
(17) HOApGpGpGpTpGpGpCpGpApTpGOH (Cd7)
(18) HOApApTpTpCpApTpCpGpCpCOH (Cd8)

EXAMPLE 5

Figure 7:
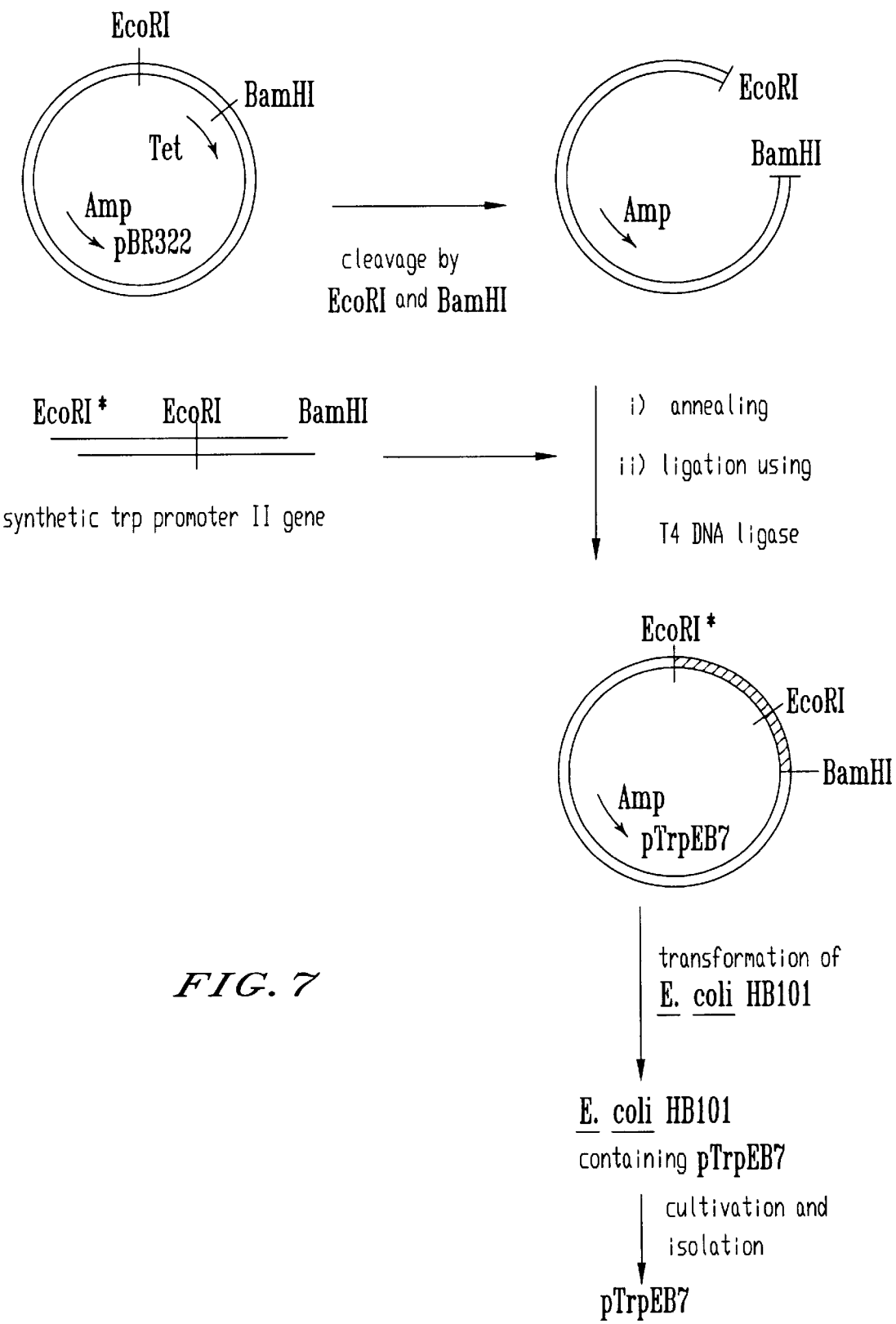

Construction and Cloning of the Synthetic trp Promoter II Gene (as Illustrated in FIG. 6 and 7)

The trp promoter II gene was constructed by the similar method as described in Example 7 (as illustrated in FIG. 6). The synthetic gene was ligated with EcoRI-BamHI fragment of pBR322 (commercially available: Takarashuzo, NEB, etc.) and then *E. coli* HB10 (ATCC 33694) was transformed with the ligation product. The plasmid obtained from the transformant of $^R$Amp and $^S$Tet was digested with HpaI to confirm a band (4.1 kbp), and then digested with BamHI to confirm a band of 90 b.p. on PAGE. Moreover, the fragment of 56 b.p. by EcoRI-BamHI digestion was confirmed by the comparison with size marker on PAGE. This plasmid was named pTrpEB7 and used construction of expression vector.

EXAMPLE 6

Figure 8:
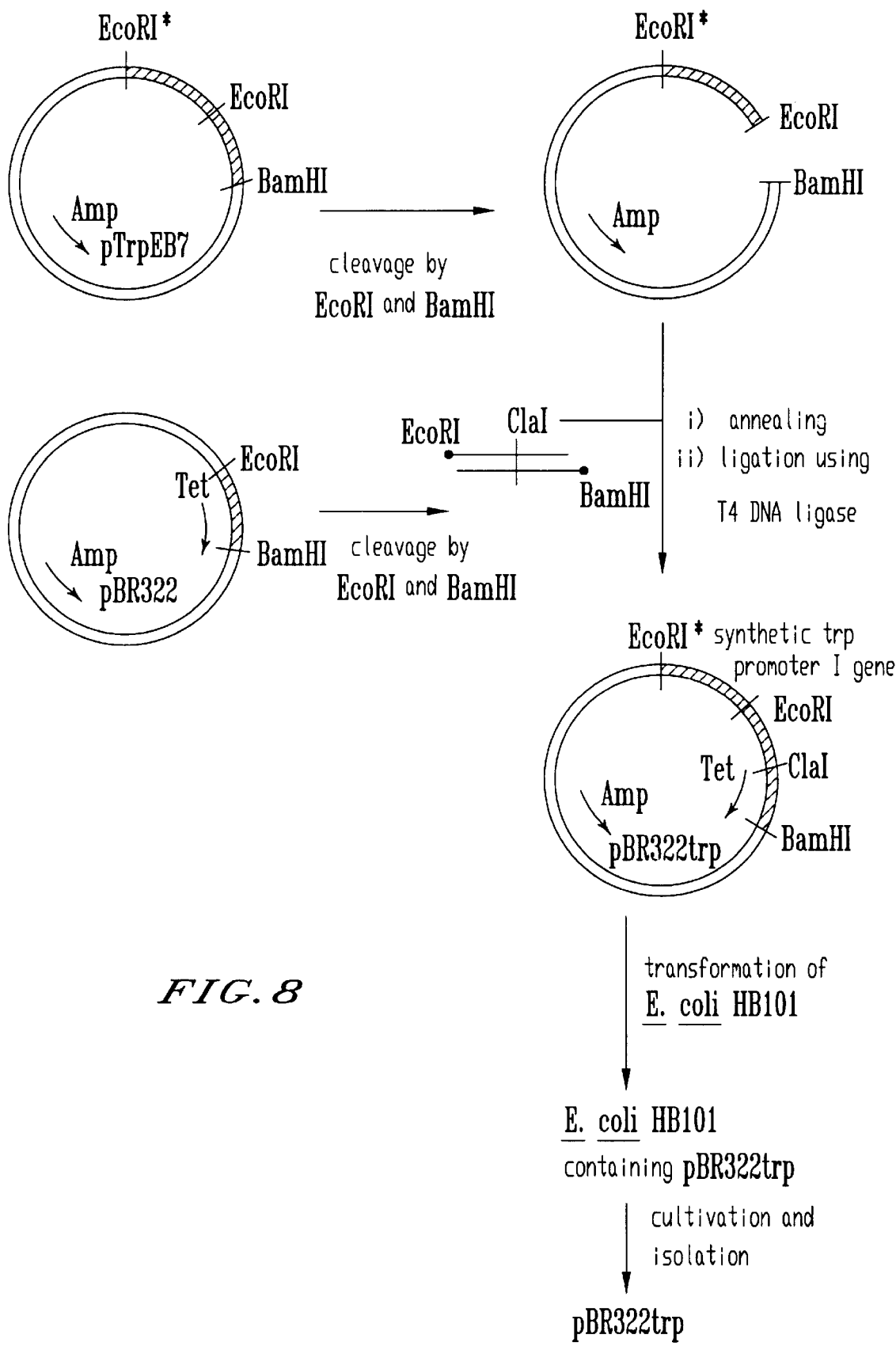

Construction and Cloning of trp Promoter Vector (pBR322trp) (as Illustrated in FIG. 8)

Plasmid pBR322 (9 μg) was digested with EcoRI and BamHI restriction endnucleases. Reaction was terminated by heating at 65° C. for 5 minutes and the fragments were separated by electrophoresis on a 0.8% agarose gel to give the small fragment (500 ng) of 375 b.p. On the other hand, plasmid pTrpEB7 (10 g) was digested with EcoRI and BamHI, followed by preparative gel electrophoresis to give the large fragment (5 μg) of 4094 b.p. The pTrpEB7 EcoRI-BamHI fragment (4094 b.p., 200 μg) was ligated with the pBR322 EcoRI-BamHI fragment (375 b.p., 100 ng) in the ligation buffer (50 mM Tris-HCl (pH 7.6), 10 mM MgCl$_2$, 20 mM DTT, 1 mM ATP, 1 mM spermidine, 50 μg/ml BSA) (20 μl) containing T4 DNA ligase (Takarashuzo: 360 unit) at 15° C. overnight. The ligated mixture was transformed into E. coli HB101 by Kushiner's method (Cf. T. Maniatis et al Molecular Cloning p252 (1982), Cold Spring Harbor Laboratory) and tetracycline resistant transformants were obtained on the plate containing tetracycline (25 μg/ml). The plasmid pBR322trp isolated from the transformant was digested with EcoRI-BamHI (375 b.p., 4094 b.p.) and HpaI (4469 b.p.) to confirm the trp promoter gene by 7.5% PAGE and 0.8% agarose gel electrophoresis.

EXAMPLE 7

Figure 9:
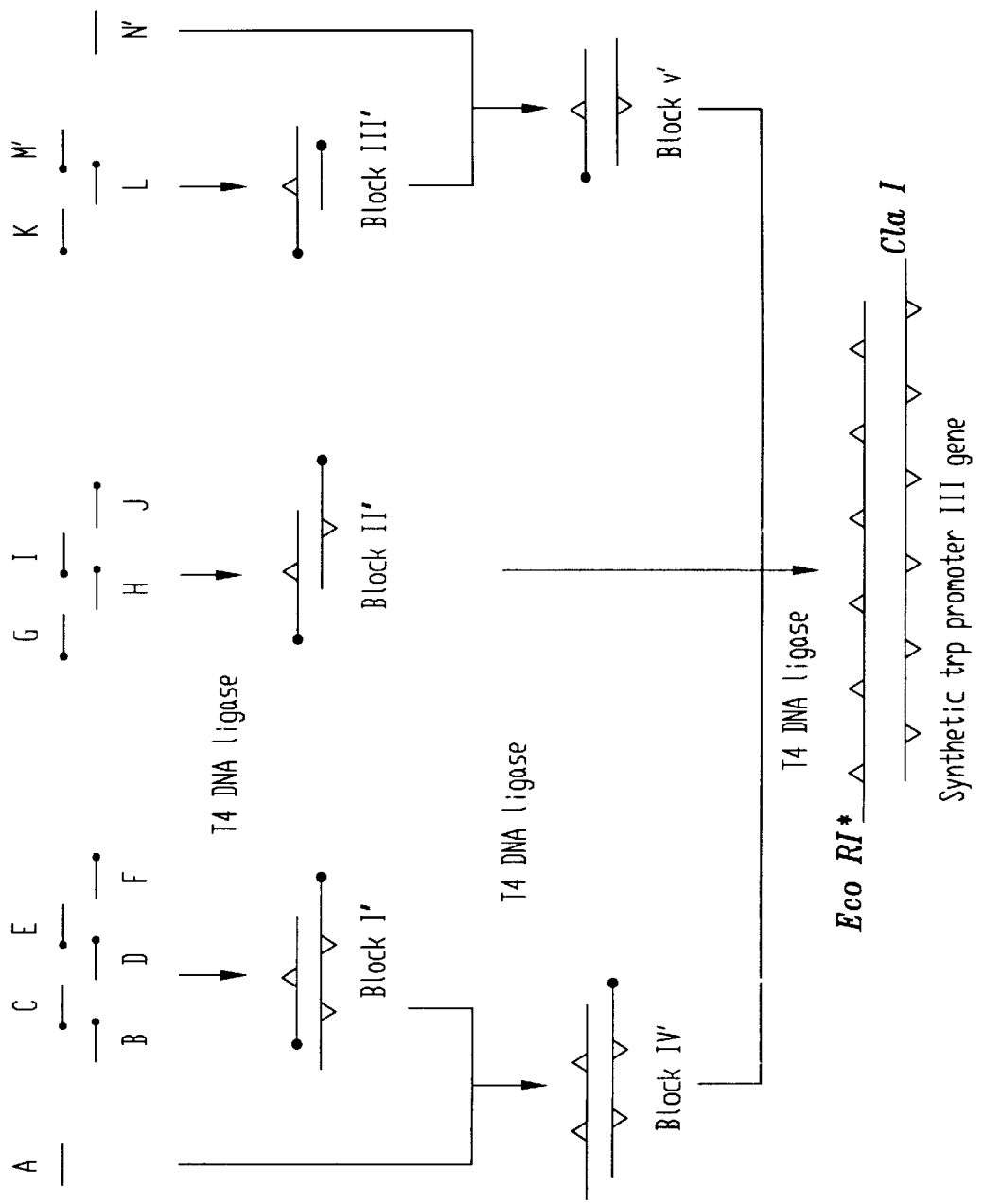

Construction of the Synthetic trp Promoter III Gene (as Illustrated in FIG. 9)

Each oligonucleotides (B-M') (each 0.2 n mole) of block I', II' and. III' were phosphorylated with T4 polynucleotide kinase (BRL; 2.5 unit) in the ligation buffer (70 μl) at 37° C. for 1 hour. To the reaction mixture of each blocks T4 DNA ligase (300 unit) and 20 mM ATP (2 μl) were added, and the mixture was incubated at 15° C. for 30 minutes. The reaction was terminated by heating at 65° C. for 10 minutes. The reaction mixture of these blocks (I', II' and III') was put together and mixed with unphosphorylated oligonucleoties (A, N') in the presence of T4 DNA ligase (360 unit) and 20 mM ATP (2 μl). After the incubation of the mixture at 15° C. for 1 hour, the last ligation product was purified by 2–16% gradient polyacrylamide gel electrophoresis (PAGE) to give the 106 b.p. synthetic trp promoter III gene.

EXAMPLE 8

Figure 10:
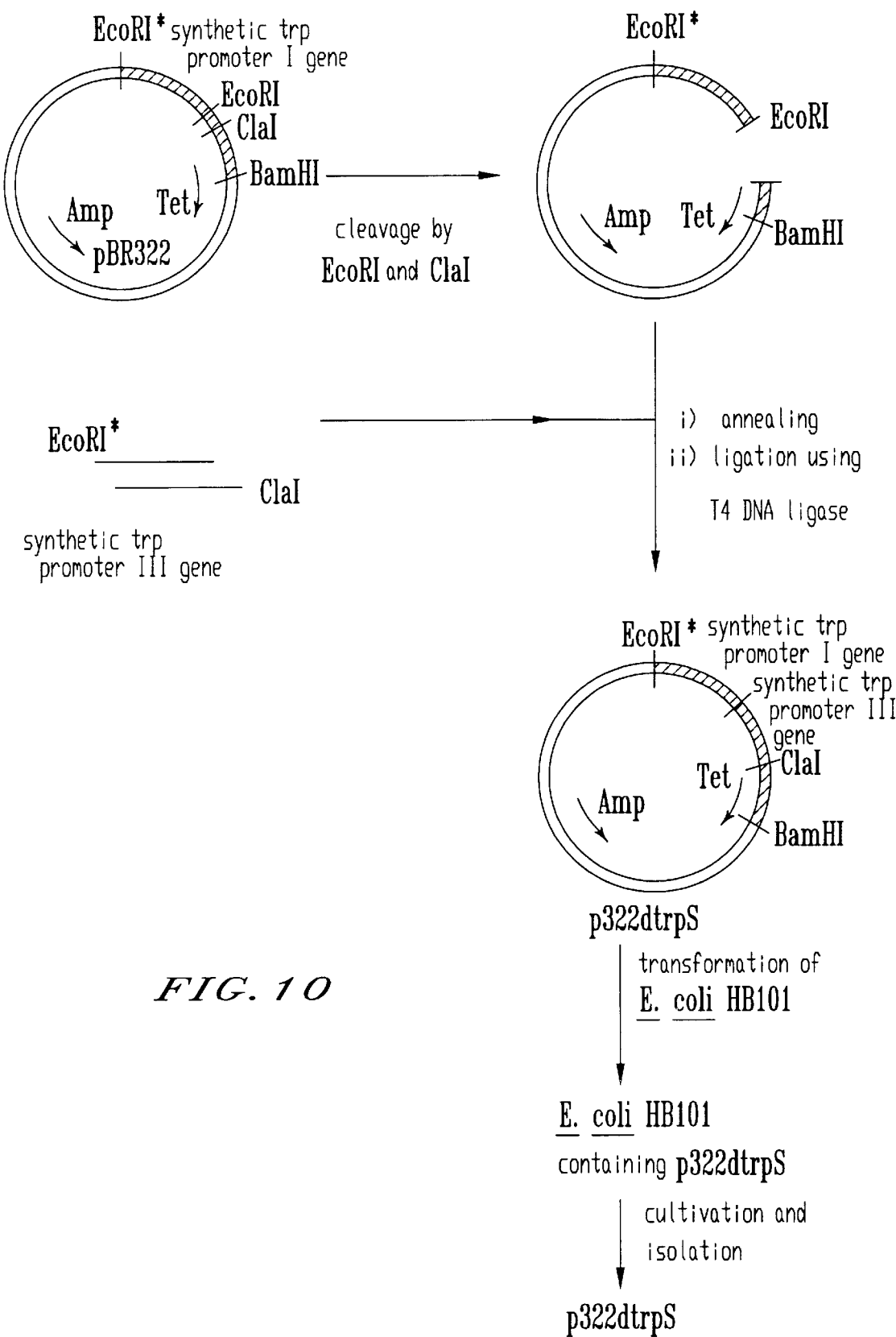

Construction and Cloning of Double trp Promoter Vector (p322dtrpS) (as Illustrated in FIG. 10)

Plasmid pBR322trp was digested with EcoRI and ClaI, followed by preparative agarose gel electrophoresis to give the large fragment of 4446 b.p. This fragment (4446 b.p.) was ligated with trp promoter III gene (106 b.p.) obtained in Example 7 in the presence of T4 DNA ligase. The ligated mixture was transformed into E. coli HB101 to give the transformants of ampicillin and tetracycline resistance. The plasmid p322dtrpS obtained from the transformant was confirmed by restriction endonuclease analysis ClaI-BamHI (352 b.p.), HpaI (107 b.p.) and AatII-ClaI (287 b.p.).

EXAMPLE 9

Figure 11:
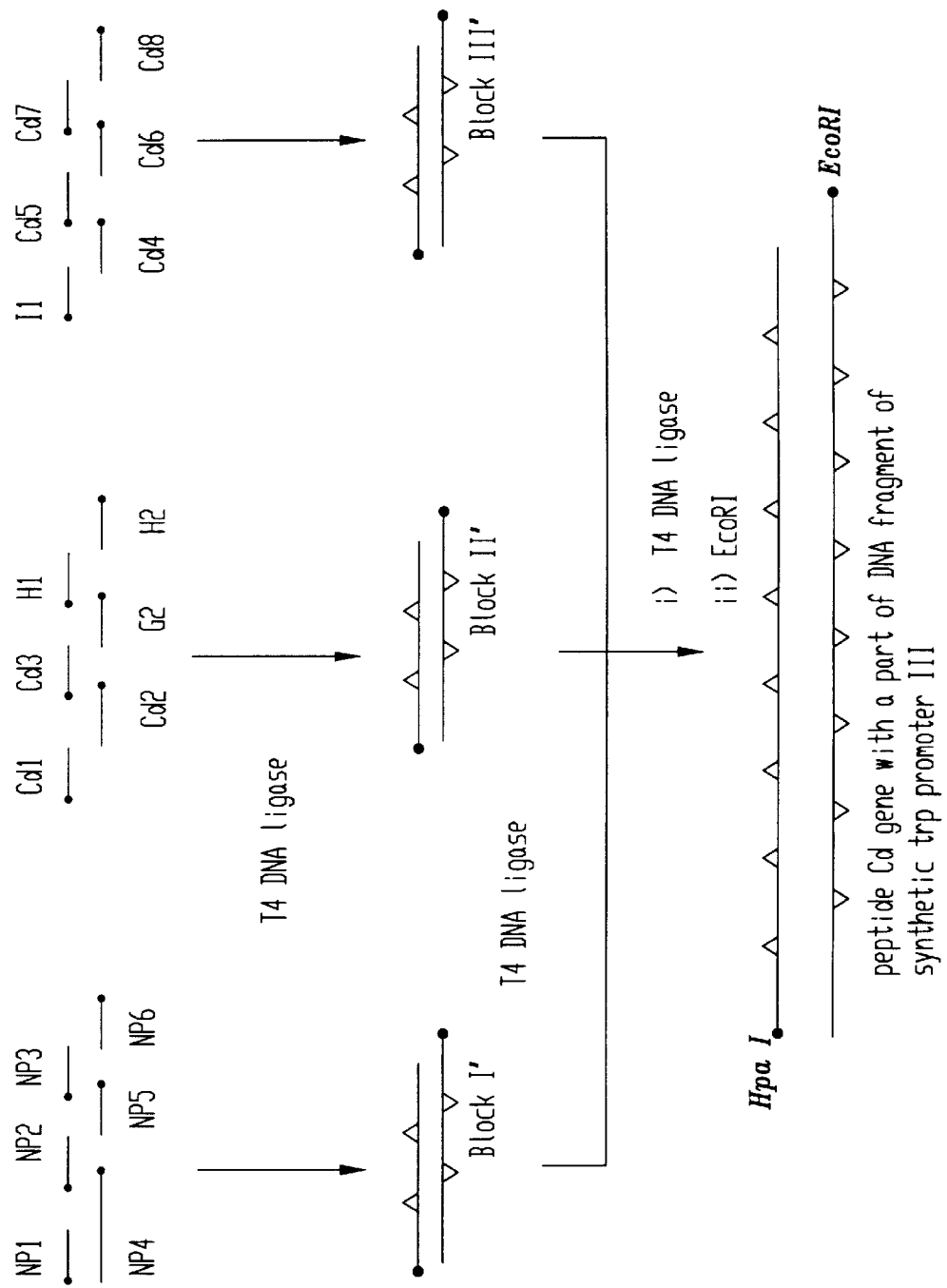

Construction of Peptide Cd Gene with a Part of DNA Fragment of Synthetic trp Promoter III (as Illustrated in FIG. 11 and 12)

Each oligonucleotides (0.2n mole) (Np1-Cd8, shown in Example 4) of block I", II" and III' were phosphorylated with T4 polynucleotide kinase (2.5unit) in ligation buffer (60 μl) at 37° C. for 1 hour. To the reaction mixture of each block T4 DNA ligase (360 unit) and ATP (2 μl) was added, the mixture was incubated at 15° C. for 1 hour. The reaction mixture of these blocks (I", II" and III') was put together and incubated with T4 DNA ligase (360 unit) and 20 mM ATP (2 μl) at 15° C. overnight, and then heated at 80° C. for 10 minutes. To the mixture 500 mM NaCl (20 μl) and EcoRI (20 unit) were added. After the incubation at 37° C. for 2 hours, the last ligation product was purified by 15% PAGE to give the peptide Cd gene with a part of DNA fragment of synthetic trp promoter III (125 b.p.), DNA sequence of which is illustrated in FIG. 12.

EXAMPLE 10

Figure 13:
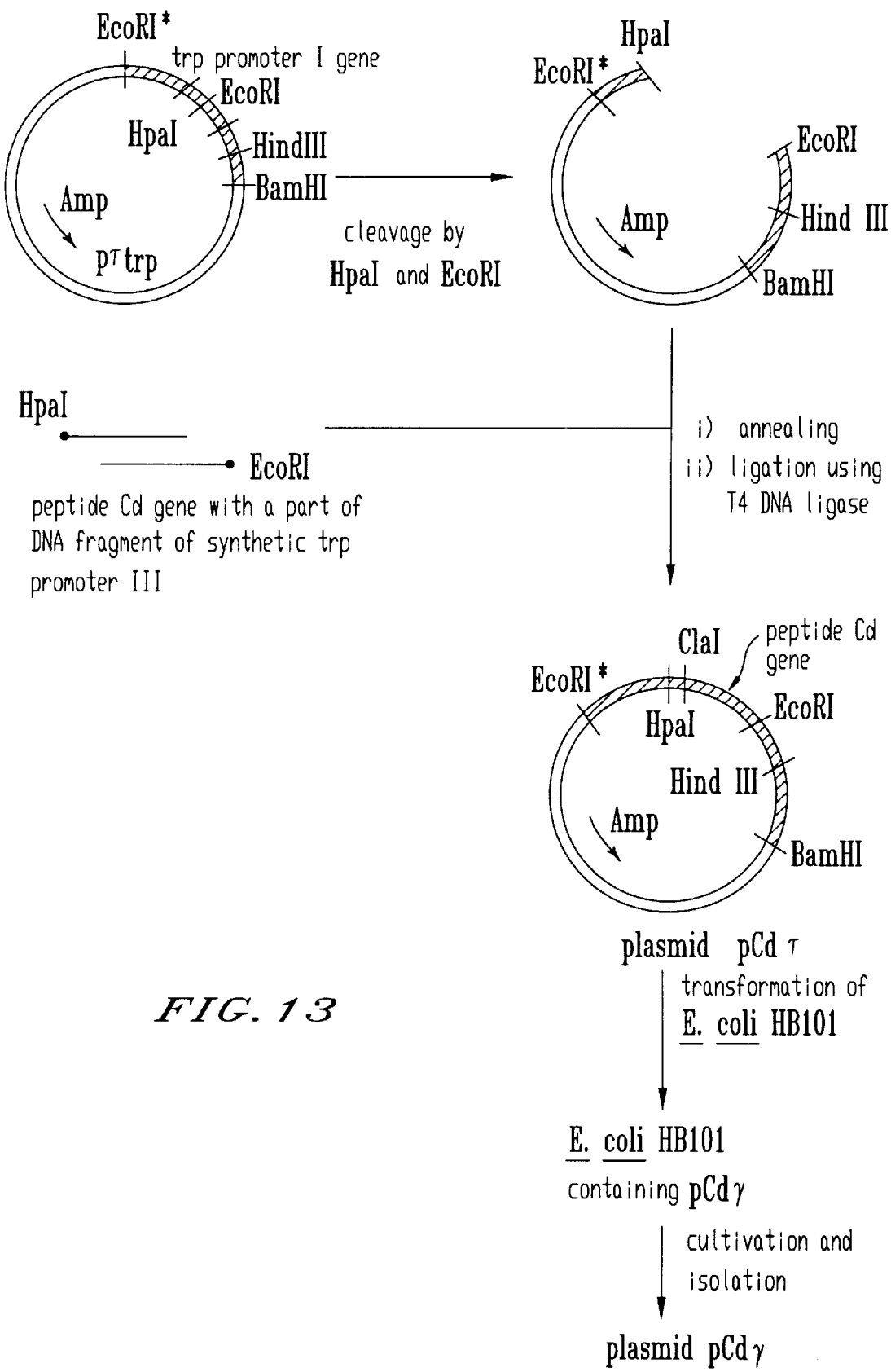

Construction and Cloning of Plasmid pCdγ (as Illustrated in FIG. 13)

Plasmid pγtrp(4544 b.p.) (Cf. GB2164650A published on Mar. 26, 1986; Escherichia coli F-9 containing this plasmid pγtrp has been depositing with FRI (Japan) under the number FERM BP-905 from Sep. 20, 1984) was digested with HpaI and EcoRI to give a large fragment (4510 b.p.), which was ligated with the peptide Cd gene with a part of DNA fragment of synthetic trp promoter III (125 b.p.) as obtained in Example 9 in the presence of T4 DNA ligase. The ligated mixture was transformed into E. coli HB101. The plasmid (pcdy) obtained from the transformant of $^R$Amp was confirmed by restriction endonuclease analysis:

ClaI-BamHI (543 b.p.), ClaI-HindIII (273 b.p.), ClaI-EcoRI (93 b.p.) and AatII-ClaI (180 b.p.).

EXAMPLE 11

Figure 14:
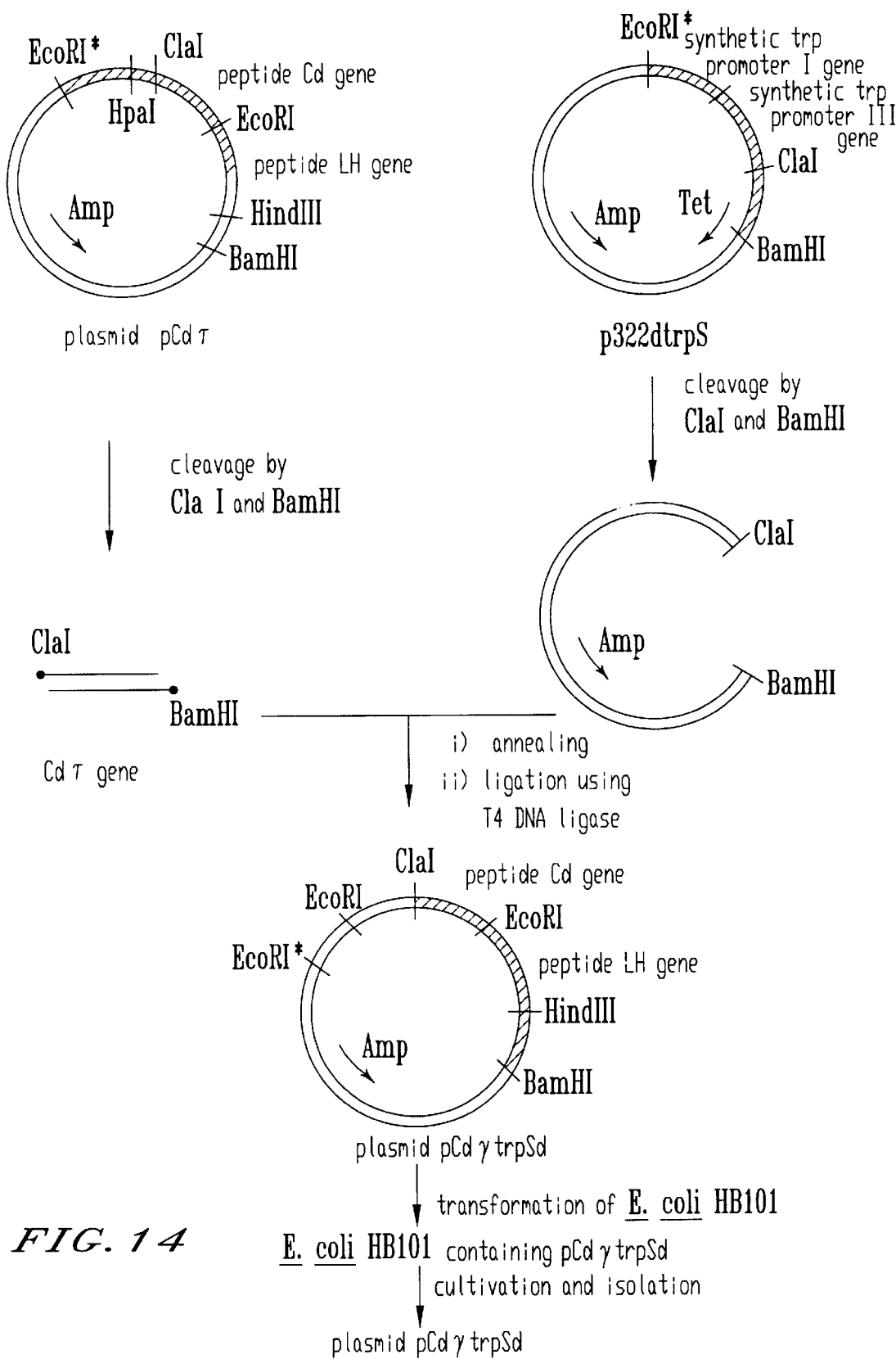

Construction and Cloning of Plasmid pCdγtrpSd (as Illustrated in FIG. 14)

The plasmid pCdγ was digested with ClaI and BamHI to give the smaller fragment (543 b.p.), which was ligated with the ClaI-BamHI fragment (4223 b.p.) of p322dtrpS (Example 7) in the presence of T4 DNA ligase. The ligated mixture was transformed into E. coli HB101. The plasmid (pCdγtrpSd) obtained from the transformant of $^R$Amp was confirmed by restriction endonuclease analysis:

HpaI-BamHI (107,575 b.p.), ClaI-BamHI (543 b.p.), PstI-EcoRI (1057 b.p.), EcoRI-BamHI (450 b.p.) HindIII-BamHI (270 b.p.), ClaI-HindIII (273 b.p.).

EXAMPLE 12

Figure 15:
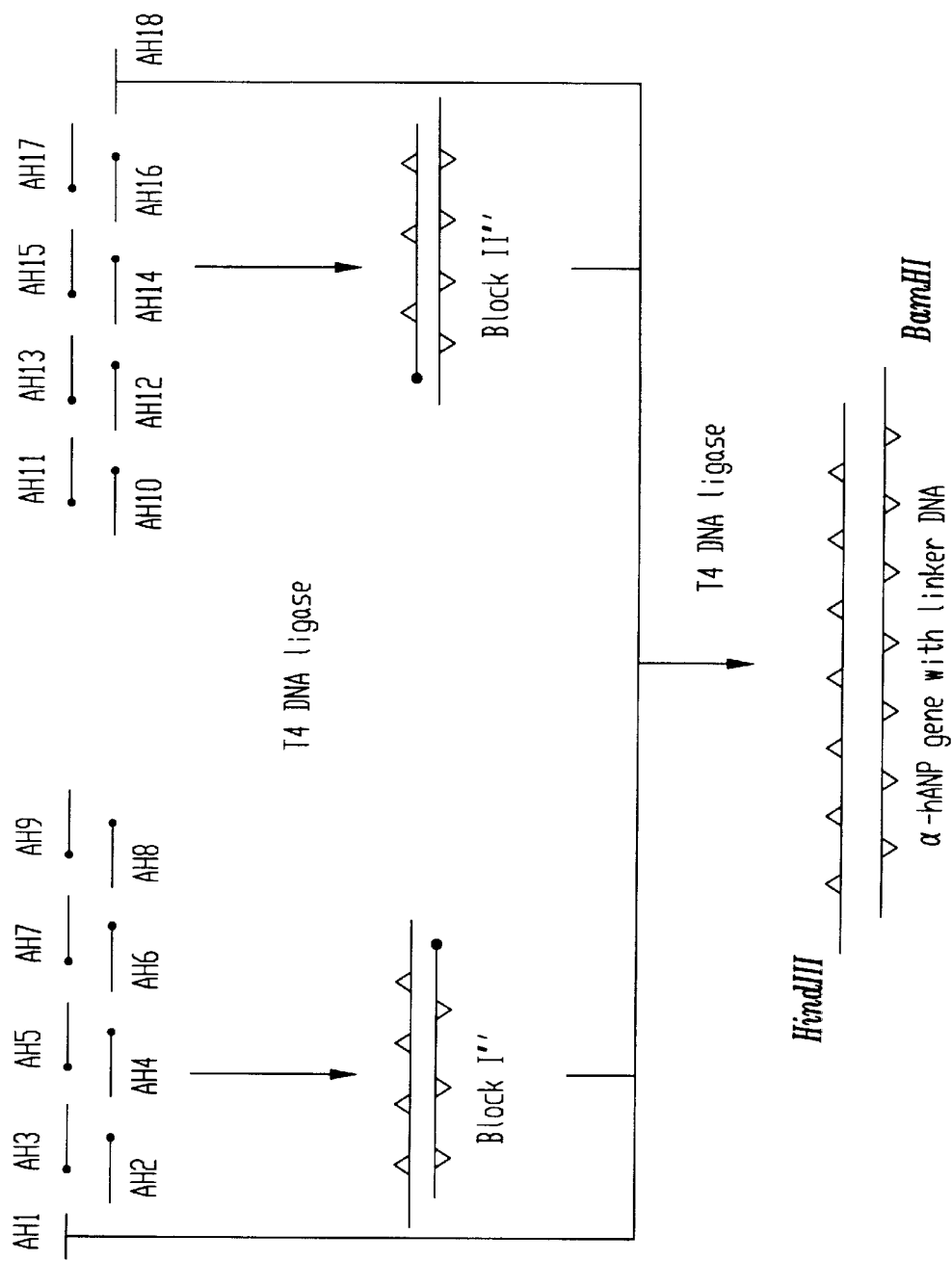

Preparation of α-hANP Gene with Linker DNA (as Illustrated in FIG. 15)

Each oligonucleotides (AH2-AH17) (each 0.2 n mole) of block I'" and II'" were phosphorylated with T4 polynucleotide kinase (2.5 unit) in the ligation buffer (70 μl) at 37° C. for 1 hour. To the reaction mixture of each blocks T4 DNA ligase (300 unit) and 20 mM ATP (2 μl) were added, and the mixture was incubated at 15° C. for 30 minutes. The reaction was terminated by heating at 65° C. for 10 minutes. The reaction mixture of two blocks (I'"and II'") was put together and mixed with unphosphorylated oligonucleotides (AH1, AH18) in the presence of T4 DNA ligase (300 unit) and 20 mM ATP (2 μl). After the incubation of the mixture at 15° C. for 1 hour, the last ligation product was purified by 2–16% gradient PAGE to give the 134 b.p. α-hANP gene with linker DNA (as illustrated in FIG. 5).

EXAMPLE 13

Figure 16:
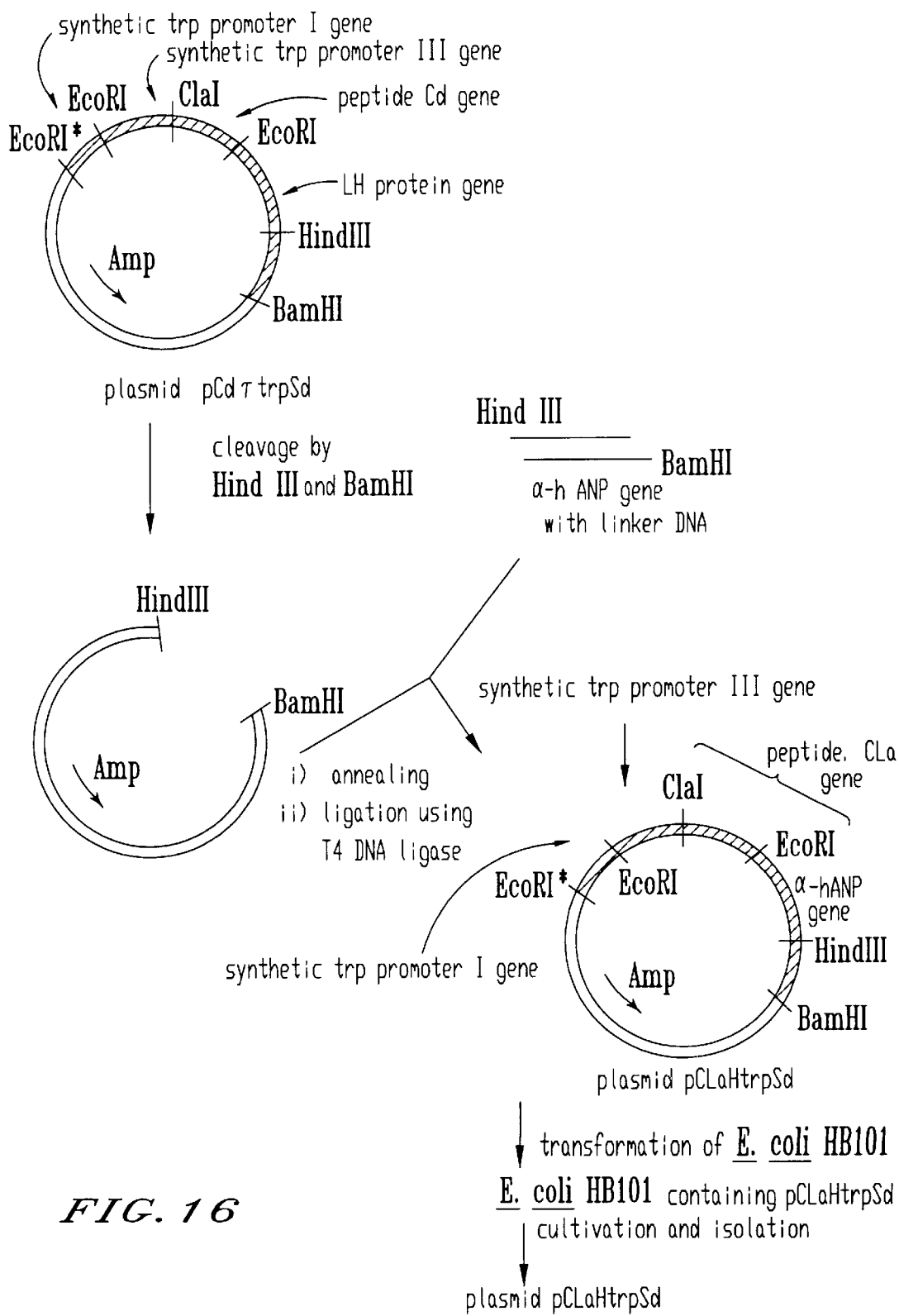

Construction and Cloning of α-hANP Expression Vector pCLaHtrpSd (as Illustrated in FIG. 16)

The plasmid pCdγtrpSd was digested with HindIII and BamHI to give the larger fragment (4743 b.p.), which was ligated with the α-hANP gene with linker DNA (134 b.p.) in the presence of T4 DNA ligase. The ligated mixture was transformed into *E. coli* HB101 to give a transformant H1. The plasmid (pCLaHtrpsd) (which contains CLaH protein (peptide CLa-fused α-hANP protein)gene, DNA sequence of which is illustrated in FIG. 17) obtained from the transformant of $^R$Amp(*E. coli* H1) was confirmed by restriction endonuclease analysis:

AatII-ClaI (287 b.p.), ClaI-BamHI (407 b.p.), ClaI-EcoRI (93, 198 b.p.), EcoRI-BamHI (116, 198 b.p.), HindIII-BamHI (134 b.p.), HpaI-BamHI (107, 439 b.p.).

EXAMPLE 14

Expression of a Gene Coding for the Peptide CLa-Fused α-hANP (CLaH Protein)

An overnight culture of *E. coli* H1 containing the expression vector, plasmid pCLaHtrpSd in L broth (20 ml) containing 50 µg/ml ampicillin was diluted in M9 medium (400 ml) containing 0.2% glucose, 0.5% casamino acid (acid-hydrolyzed casein), 50 µg/ml vitamin B1 and 25 µl/ml ampicillin, and the *E. coli* was cultured at 37° C. When A600 (absorbance at 600 nm) of the cultured broth was 0.5, β-indole acrylic acid (2 mg/ml ethanol; 2 ml) was added and the cells were incubated for 3 hours (final A600=1.85). Then the cells were harvested by centrifugation (6000 rpm, 4° C., 5 minutes).

EXAMPLE 15

Isolation and Purification of α-hANP (1) Isolation and Purification of the Peptide CLa-Fused α-hANP (CLaH Protein)

The wet cell paste from the culturedbroth (600 ml) as prepared in Example 14 was suspended in 8 ml of 10 mM PBS-EDTA (pH7.4) (NaCl (8.0 g), KCl (0.2 g), Na2HPO4 12H$_2$O (2.9 g), KH$_2$PO$_4$ (0.2 g), EDTA (3.73 g)/liter) and cells were destroyed by sonication at 0° C. The pellet was collected by centrifugation at 15,000 rpm for 20 minutes (4° C.), and suspended in 8 ml of 6M guanidine-HCl, 10 mM PBS-EDTA and 2 mM β-mercaptoethanol and the suspension was treated by super sonication at 0° C. The suspension was centrifuged at 15,000 rpm for 20 minutes (4° C.) and the supernatant was dialyzed overnight at 40C against 10 mM pBS-EDTA solution containing p-nitrophenyl methylsulfonyl fluoride (PMSF). After the fraction dialyzed was centrifuged (15,000 rpm, 4° C., 20 minutes), the pellet was dissolved in 100 mM Tris-HCl buffer (pH8.0) (8 ml) containing 6M quanidine-HCl, 10 mM EDTA and 100 mM dithiothreitol and the solution was stood overnight. The solution was dialyzed against 1M acetic acid (0.5 liters) containing 10 mM 2-mercaptoethanol twice and adjusted to pH8.0 with trisaminomethane. The resulting precipitate (fused protein; 15.2 mg) was collected by centrifugation (3.000 rpm 10 minutes), and washed with 10 mM sodium acetate buffer (pH5.0).

(2) Elimination of Peptide CLa from the Peptide CLa Fused α-hANP with Achromobacter Protease I(API):

The fused protein obtained above was suspended in 10 mM sodium acetate buffer (pH5.0) (30 ml) containing 8M urea, the suspension was incubated with Achromobactor protease I(API) (0.25 unit) (Wako pure chemical industries, Ltd) at 37° C. for 2 hours. The reaction mixture was diluted with distilled water (30 ml), adjusted to pH9.0 with trisaminomethane, and then incubated with additional API (0.25 unit) at 37° C. for 2 hours. The reaction solution was diluted with 10 mM sodium phosphate buffer (pH7.0) (120 ml), and adjusted to pH7 with acetic acid. The solution was applied to a Sp-sephadex C-25 column (15 ml) equilibrated with 10 mM sodium phosphate buffer (pH7.0). The column was washed with the same buffer, and eluted with 10 mM sodium phosphate buffer (pH8.0) containing 0.5M aqueous sodium chloride to collect the fractions containing a partial purified α-hANP (0.4 mg).

(3) High Performance Liquid Chromatography (HPLC):

The pooled fraction obtained in the above (2) was concentrated in vacuo, dialyzed against water (300 ml), and purified by reverse phase HPLC to give a pure α-hANP (0.3 mg).

HPLC Condition (preparation)

column: Beckman Ultrapore semi-prep. (φ10×250 mm)

flow rate: 2.5 ml/minute elution: linear gradient from 10% to 60% acetonitrile in 0.01M trifluoroacetic acid over 50 minutes.

monitor absorbance at 214 nm (analysis)

column: Beckmann Ultrapore RPSC (φ4.6×75 mm)

flow rate: 1 ml/minute elution: same condition as the preparation retention time: 11.9 minutes The α-hANP was supperimposed with authentic α-hANP (sold by Funakoshi)

(4) Amino Acid Analysis of α-hANP

The sample was reduced and carboxymethylated, and then hydrolyzed with 6N HCl at 110° C. for 24 hours. The amino acid composition of α-hANP was obtained using a Waters amino acid analysis system.

Amino acid compositions (residues per mole) of α-hANP were coincided with the expected values.

(5) Amino Acid Sequence Analysis of α-hANP

The N-terminal amino acid sequence of α-hANP was determined by Edman's method (DABITC method) [described in FEBS Lett., 93,205 (1978)] to confirm N-terminal Ser and Leu sequence. C-terminal amino acids (Ser-Phe-Arg-Tyr) were determined by the digestion with carboxypeptidase and the followed amino acid analysis using a Waters amino acid analysis system. The whole amino acid sequence of α-hANP obtained in the above Example was determined by using both procedures and was identical with the known sequence of α-hANP.

EXAMPLE 16

Figure 18:
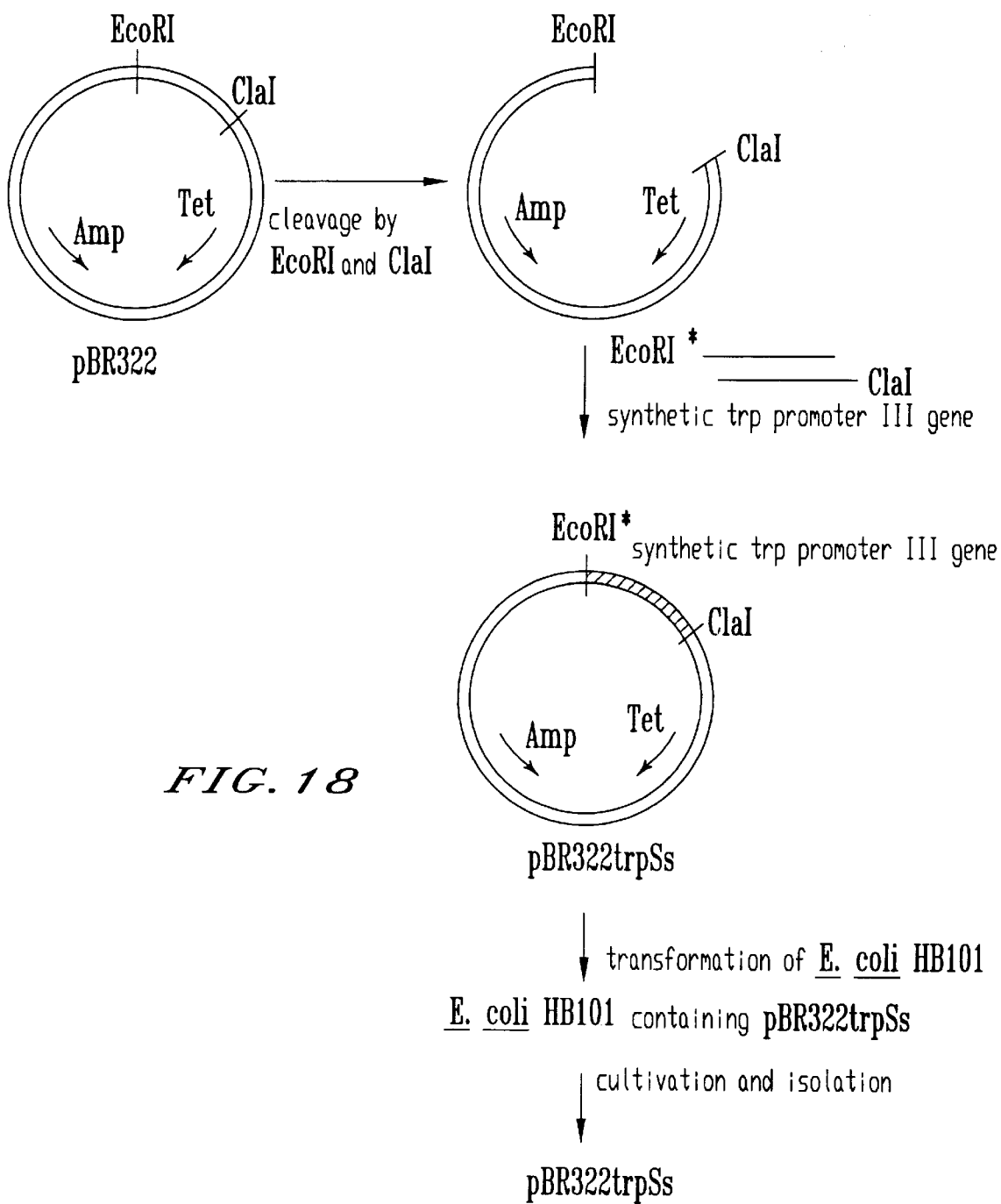

Construction and Cloning of Plasmid pBR322trpSs (as Illustrated in FIG. 18)

Plasmid pBR322 was digested with EcoRI and ClaI. The large fragment (4340 bp) was purified by 0.8% agarose gel electrophoresis, and ligated to the synthetic trp promoter III gene in the presence of T4 DNA ligase and 1 mM ATP. The ligation mixture was used to transform *E. coli* HB101. The plasmid DNA (pBR322trpSs) was isolated from a transformed clone ($^R$Amp) and characterized by restriction endonuclease analysis.

Analysis data: Hpa I; 4445 bp, ClaI-Pst I; 834 bp

EXAMPLE 17

Figure 19:
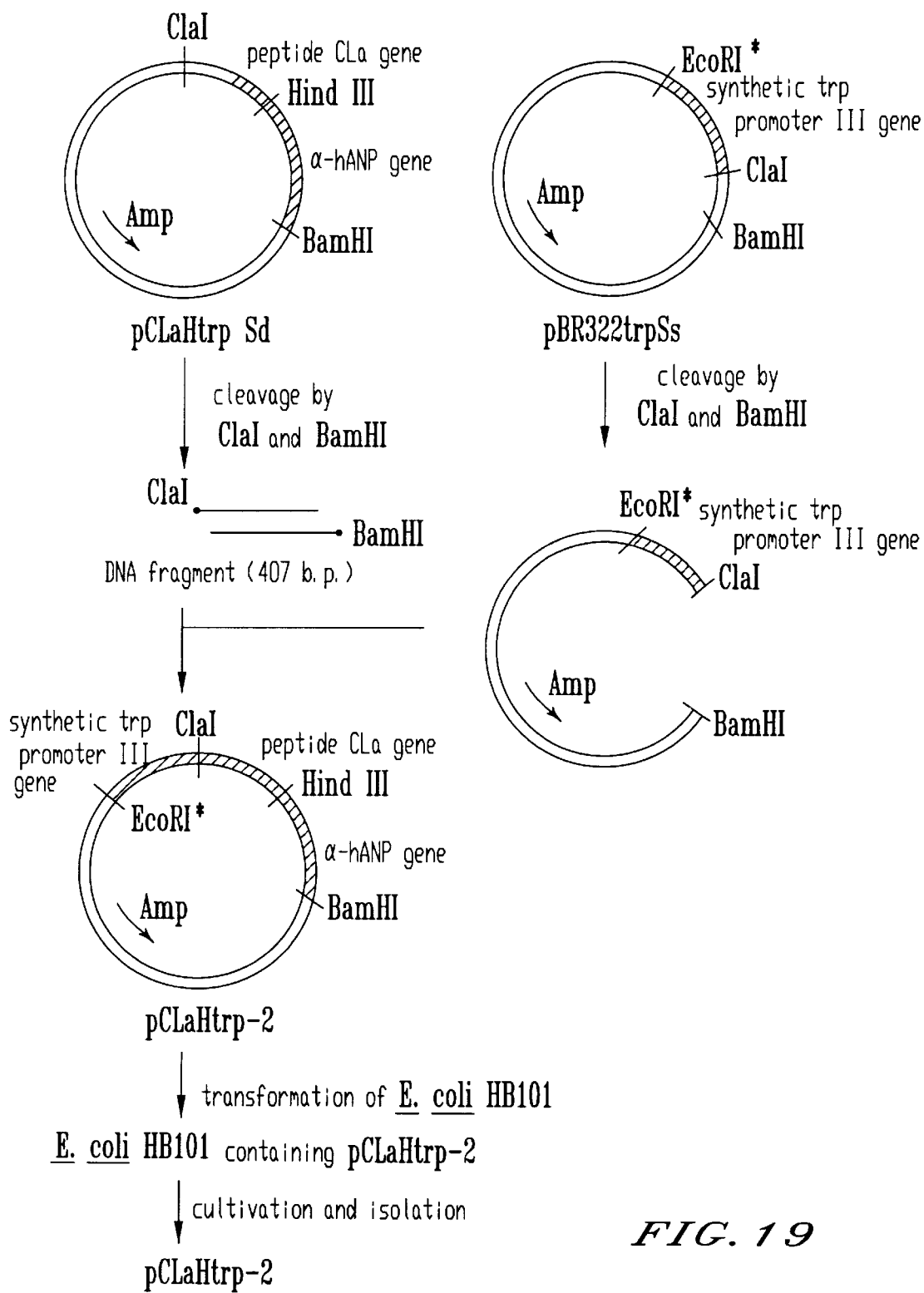

Construction and Cloning of Plasmid pCLaHtrp-2 (as Illustrated in FIG. 19)

Plasmid pCLaHtrpSd was digested with ClaI and BamHI. The small fragment (407 bp) was isolated. On the other hand pBR322trpSs was digested with ClaI and BamHI. The larger fragment (4093 bp) was isolated and ligated to the former DNA (407 bp). After transformation of E. coli HB101 with the ligation mixture, the desired plasmid (pCLaHtrp-2) was isolated from a transformed clone ($^R$Amp) and characterized by restriction enzyme analysis: ClaI-Pst I; 834 bp, ClaI-BamHI; 407 bp

EXAMPLE 18

Synthesis of Oligonucleotides

Following oligonucleotides were prepared in a similar manner to that of Example 1.

(1) HOGpApTpCpCpTpCpGpApGpApTpCpApAOH (T1)
(2) HOGpCpCpTpTpTpApApTpTpGpApTpCpTpCpGpApGOH (T2)
(3) HOTpTpApApApGpGpCpTpCpCpTpTpTpTpGpGpApAOH (T3)
(4) HOApApApApApGpGpCpTpCpCpApApApApGpGpAOH (T4)
(5) HOGpCpCpTpTpTpTpTpTpTpTpTpGOH (T5)
(6) HOTpCpGpApCpApApApApApAOH (T6)

EXAMPLE 19

Figure 20:
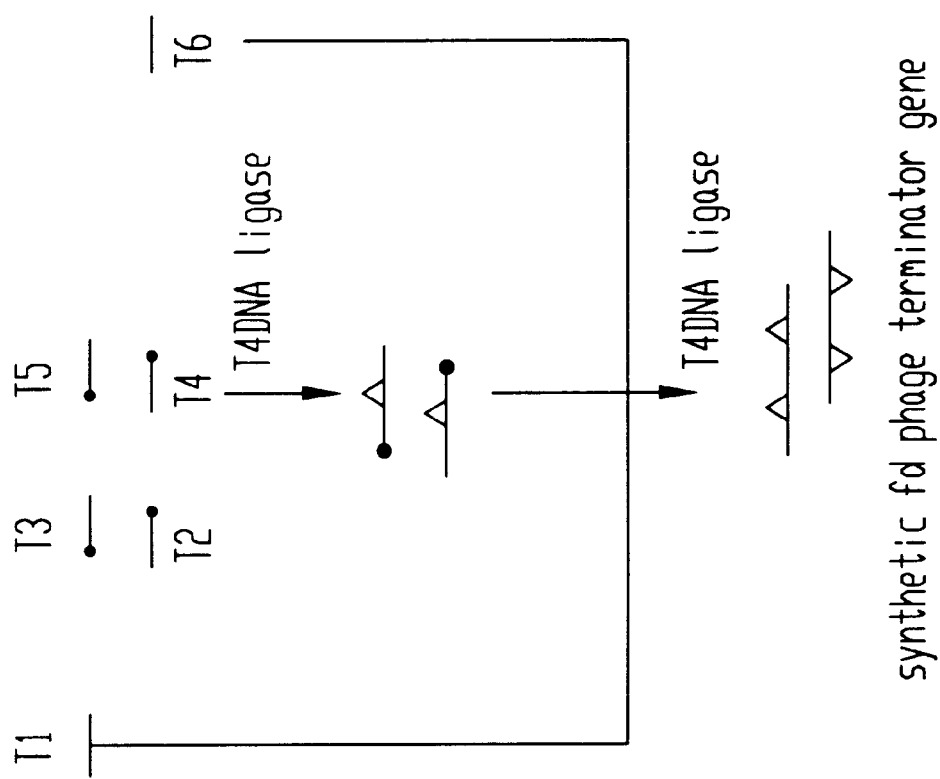
Figure 21:
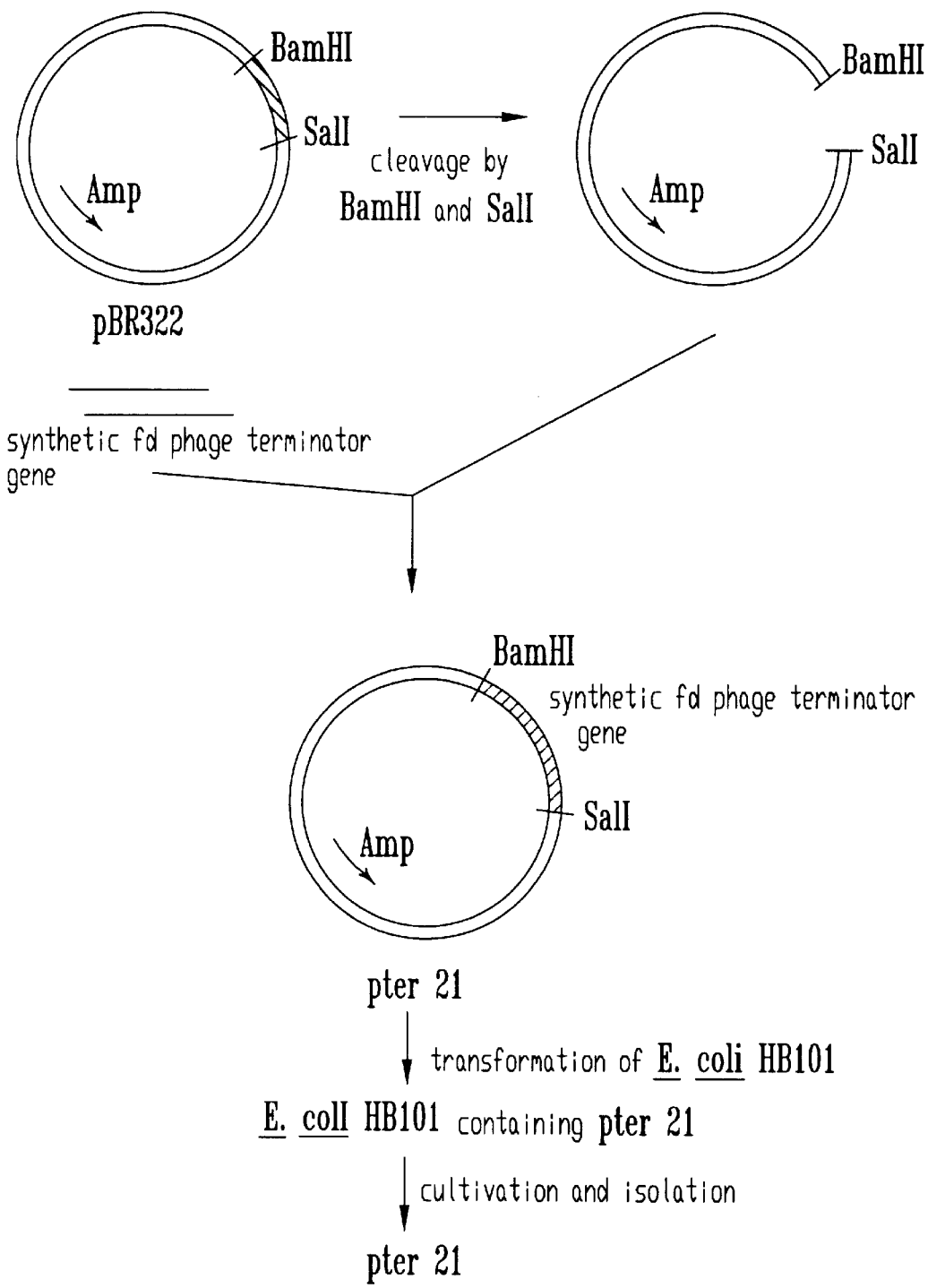

Construction and Cloning of Synthetic fd Phage Terminator (as Illustrated in FIG. 20 and 21)

The synthetic fd phage terminator was constructed by a similar method as described in Example 7 (as illustrated in FIG. 20).

Namely, DNA oligomers T2, T3, T4 and T5 (each 0.4 nmole) were mixed and phosphorylated with T4 polynucleotide kinase in the presence of 1 mM ATP. The reaction mixture was heated at 65° C. for 10 minutes to inactivate the enzyme. To the resultant mixture, DNA oligomer T1 and T6 (each 0.8 nmole) and T4 DNA ligase were added. The mixture was incubated at 15° C. for 30 minutes, and applied to 2→16% gradient polyacrylamide gel electrophoresis. The desired DNA fragment (47 bp) was recovered by electroelution and ligated to the larger fragment of pBR322 digested with BamHI and Sal I (4088 bp).After transformation of E. coli HB101 with the ligation mixture, the desired plasmid (pter) was isolated from a transformed clone ($^R$Amp). Restriction enzyme analysis: BamHI-Sal I; 47 bp, Ava I; 817 bp

Figure 22:
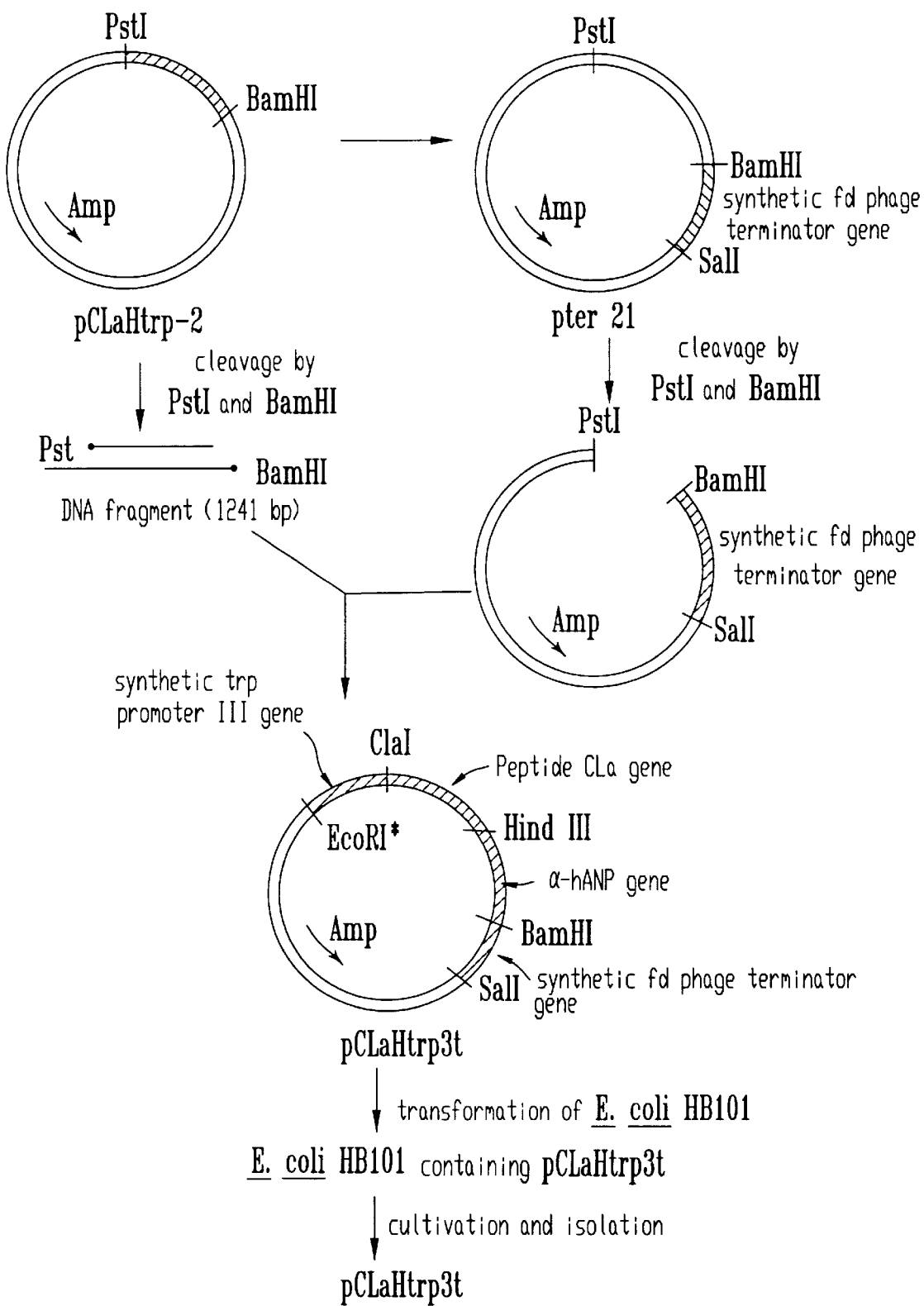

EXAMPLE 20
Construction and Cloning of α-hANP Expression Vector Plasmid pCLaHtrp3t (As Illustrated in FIG. 22)

Plasmid pCLaHtrp-2 was digested with Pst I and BamHI. From the digestion mixture, the small fragment (1241 bp) was isolated and ligated to the large fragment of pter 21 obtained from digestion of pter 21 with Pst I and BamHI (3005 bp).

The ligation mixture was transformed into E. coli HB101 to give a transformant E. coli H2. The plasmid CLaHtrp3t (which contains CLaH protein gene) obtained from the transformant of $^R$Amp (E. coli H2) was confirmed by restriction endonuclease analysis: ClaI-EcoRI; 93 bp, 198 bp, HindIII-BamHI; 134 bp, PstI-ClaI-XhoI; 834 bp, 411 bp

EXAMPLE 21

Production of α-hANP Using E. coli H2

α-hANP was obtained in a similar manner to those of Example 14 and 15 using E. coli H2 in place of E. coli H1.

Amino acid sequence of thus obtained α-hANP was identical with the known sequence of α-hANP.

We claim:

1. An isolated and purified DNA fragment, comprising a sequence of DNA which encodes a protective peptide-fused α-hANP, in which a protective peptide which has C-terminus lysine residue is fused to the N-terminus of α-hANP, wherein said α-hANP has the amino acid sequence:

```
Ser-Leu-Arg-Arg-Ser-Ser-Cys-Phe-Gly-Gly-Arg-Met
 1   2   3   4   5   6   7   8   9  10  11  12

Asp-Arg-Ile-Gly-Ala-Gln-Ser-Gly-Leu-Gly-Cys-Asn-
Ser-
 13  14  15  16  17  18  19  20  21  22  23  24  25

Phe-Arg-Tyr,
 26  27  28
```
and wherein said C-terminus lysine is fused directly to Ser at position 1 in said amino acid sequence, and
   wherein said protective peptide-fused α-hANP is cleavable to afford α-hANP.

2. The DNA fragment of claim 1, wherein said DNA sequence comprises a subsequence:

```
Coding:    5' - TCT CTG CGT AGA TCC TCT TGC TTT GGT GGC

Noncoding: 3' - AGA GAC GCA TCT AGG AGA ACG AAA CCA CCG

CGT ATG GAC CGC ATC GGT GCT CAG TCC GGT CTG GGC TGT AAC

GCA TAC CTG GCG TAG CCA CGA GTC AGG CCA GAC CCG ACA TTG

TCT TTC CGT TAC - 3'

AGA AAG GCA ATG - 5'.
```

3. The DNA fragment of claim 1, wherein said DNA sequence has the sequence of FIG. 17.

4. An isolated and purified recombinant vector, comprising a DNA sequence which encodes a protective peptide-fused α-hANP, in which a protective peptide which has C-terminus lysine residue is fused to the N-terminus of α-hANP, wherein said α-hANP has the amino acid sequence:

```
Ser-Leu-Arg-Arg-Ser-Ser-Cys-Phe-Gly-Gly-Arg-Met
 1   2   3   4   5   6   7   8   9  10  11  12
```

-continued

```
Asp-Arg-Ile-Gly-Ala-Gln-Ser-Gly-Leu-Gly-Cys-Asn-
Ser-
 13  14  15  16  17  18  19  20  21  22  23  24  25

Phe-Arg-Tyr,
 26  27  28
```
and wherein said C-terminus lysine residue is fused directly to Ser at position 1 of said amino acid sequence, and wherein said protective peptide-fused α-hANP is cleavable to afford α-hANP.

5. The recombinant vector of claim 4, wherein said DNA sequence comprises a subsequence:

```
Coding:    5' - TCT CTG CGT AGA TCC TCT TGC TTT GGT GGC

Noncoding: 3' - AGA GAC GCA TCT AGG AGA ACG AAA CCA CCG

CGT ATG GAC CGC ATC GGT GCT CAG TCC GGT CTG GGC TGT AAC

GCA TAC CTG GCG TAG CCA CGA GTC AGG CCA GAC CCG ACA TTG

TCT TTC CGT TAC - 3'

AGA AAG GCA ATG - 5'.
```

6. The recombinant vector of claim 4, wherein said DNA sequence has the sequence of FIG. 17.

7. A transformed bacterium, comprising an expression vector comprising a DNA sequence which encodes a protective peptide-fused α-hANP, in which a protective peptide which has C-terminus lysine residue is fused to the N-terminus of α-hANP, wherein said α-hANP has the amino acid sequence:

```
Ser-Leu-Arg-Arg-Ser-Ser-Cys-Phe-Gly-Gly-Arg-Met
  1   2   3   4   5   6   7   8   9  10  11  12

Asp-Arg-Ile-Gly-Ala-Gln-Ser-Gly-Leu-Gly-Cys-Asn-
Ser-
 13  14  15  16  17  18  19  20  21  22  23  24  25

Phe-Arg-Tyr,
 26  27  28
```
and wherein said C-terminus lysine residue is fused directly to Ser at position 1 in said amino acid sequence, and wherein said protective peptide-fused α-hANP is cleavable to afford α-hANP; and wherein said bacterium is *E. coli.*

8. The transformed bacterium of claim 6, wherein said DNA sequence comprises a subsequence:

```
Coding:    5' - TCT CTG CGT AGA TCC TCT TGC TTT GGT GGC

Noncoding: 3' - AGA GAC GCA TCT AGG AGA ACG AAA CCA CCG

CGT ATG GAC CGC ATC GGT GCT CAG TCC GGT CTG GGC TGT AAC

GCA TAC CTG GCG TAG CCA CGA GTC AGG CCA GAC CCG ACA TTG

TCT TTC CGT TAC - 3'

AGA AAG GCA ATG - 5'.
```

9. The transformed bacterium of claim 6, wherein said DNA sequence has the sequence of FIG. 17.

10. A process for the production of α-hANP, comprising the steps of:
   (1) culturing the transformed bacterium of claim 7, to obtain a culture broth comprising a protective peptide-fused α-hANP;
   (2) recovering said protective peptide-fused α-hANP from said culture broth; and
   (3) removing a protective peptide portion of said protective peptide-fused α-hANP in the presence of achromobacter protease I, to obtain said α-hANP.

11. The process of claim 10, wherein said transformed bacterium is the transformed bacterium of claim 8.

12. The process of claim 10, wherein said transformed bacterium is the transformed bacterium of claim 9.

* * * * *